US007918800B1

(12) United States Patent
Brown et al.

(10) Patent No.: US 7,918,800 B1
(45) Date of Patent: Apr. 5, 2011

(54) ANEURYSM SENSING DEVICES AND DELIVERY SYSTEMS

(75) Inventors: Peter S. Brown, Palo Alto, CA (US); Albert K. Chin, Palo Alto, CA (US); Arnold M. Escano, Santa Clara, CA (US); Gregory W. Fung, San Mateo, CA (US); Rasean L. Hamilton, Santa Clara, CA (US); Juan I. Perez, Sunnyvale, CA (US); Richard Rapoza, San Francisco, CA (US); Shuji Uemura, San Francisco, CA (US); Michael F. Wei, Menlo Park, CA (US); Arlene S. Yang, Belmont, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 1410 days.

(21) Appl. No.: 10/962,206

(22) Filed: Oct. 8, 2004

(51) Int. Cl.
*A61B 5/02* (2006.01)
*A61B 5/00* (2006.01)
*A61B 17/08* (2006.01)

(52) U.S. Cl. ........ 600/481; 600/300; 606/213; 606/215; 606/216

(58) Field of Classification Search .................. 600/481, 600/483, 485, 486, 488, 561, 300; 604/503, 604/505; 606/213–216
See application file for complete search history.

(56) References Cited

U.S. PATENT DOCUMENTS

| | | | |
|---|---|---|---|
| 2,634,721 A | 5/1951 | Greenwood, Jr. | |
| 3,240,207 A | 3/1966 | Barker et al. | |
| 3,665,916 A * | 5/1972 | Kobayashi et al. | 600/436 |
| 3,888,708 A | 6/1975 | Wise et al. | |
| 3,911,902 A * | 10/1975 | Delpy | 600/488 |
| 4,732,874 A | 3/1988 | Sparks | |
| 4,815,472 A | 3/1989 | Wise et al. | |
| 4,834,101 A | 5/1989 | Collison et al. | |
| 4,846,191 A | 7/1989 | Brockway et al. | |
| 4,881,410 A | 11/1989 | Wise et al. | |
| 4,953,387 A | 9/1990 | Johnson | |
| 5,000,049 A | 3/1991 | Cooper et al. | |
| 5,013,396 A | 5/1991 | Wise et al. | |
| 5,055,838 A | 10/1991 | Wise et al. | |
| 5,059,543 A | 10/1991 | Wise et al. | |
| 5,100,479 A | 3/1992 | Wise et al. | |
| 5,113,868 A | 5/1992 | Wise et al. | |
| 5,207,103 A | 5/1993 | Wise et al. | |
| 5,213,999 A | 5/1993 | Sparks et al. | |
| 5,250,461 A | 10/1993 | Sparks | |
| 5,250,837 A | 10/1993 | Sparks | |
| 5,262,127 A | 11/1993 | Wise et al. | |
| 5,296,255 A | 3/1994 | Gland et al. | |
| 5,314,458 A | 5/1994 | Najafi et al. | |
| 5,343,064 A | 8/1994 | Spangler et al. | |

(Continued)

FOREIGN PATENT DOCUMENTS

EP 0 646 365 A1 4/1995

(Continued)

*Primary Examiner* — Charles A Marmor, II
*Assistant Examiner* — Navin Natnithithadha
(74) *Attorney, Agent, or Firm* — Brooks, Cameron & Huebsch PLLC

(57) ABSTRACT

A system for gaining access to an interventional site within vasculature through a vessel wall or other structure such as that of a medical device. An apparatus is provided to accomplish a sealed worksite as are sensor delivery systems including sealable sensor devices that are adapted to be placed at the interventional site.

10 Claims, 26 Drawing Sheets

U.S. PATENT DOCUMENTS

| | | | |
|---|---|---|---|
| 5,377,524 A | 1/1995 | Wise et al. | |
| 5,385,709 A | 1/1995 | Wise et al. | |
| 5,411,551 A | 5/1995 | Winston et al. | |
| 5,417,235 A | 5/1995 | Wise et al. | |
| 5,427,975 A | 6/1995 | Sparks et al. | |
| 5,531,121 A | 7/1996 | Sparks et al. | |
| 5,547,093 A | 8/1996 | Sparks | |
| 5,567,989 A | 10/1996 | Sim | |
| 5,598,847 A | 2/1997 | Renger | |
| 5,663,508 A | 9/1997 | Sparks | |
| 5,676,696 A | 10/1997 | Marcade | |
| 5,706,565 A | 1/1998 | Sparks et al. | |
| 5,719,069 A | 2/1998 | Sparks | |
| 5,735,887 A | 4/1998 | Barreras, Sr. et al. | |
| 5,756,900 A | 5/1998 | Arie et al. | |
| 5,807,258 A | 9/1998 | Cimochowski | |
| 5,831,162 A | 11/1998 | Sparks et al. | |
| 5,875,782 A * | 3/1999 | Ferrari et al. | 128/898 |
| 5,906,631 A * | 5/1999 | Imran | 606/213 |
| 5,910,155 A * | 6/1999 | Ratcliff et al. | 606/213 |
| 5,915,281 A | 6/1999 | Sparks | |
| 5,929,497 A | 7/1999 | Chavan et al. | |
| 5,932,809 A | 8/1999 | Sparks et al. | |
| 5,936,164 A | 8/1999 | Sparks et al. | |
| 5,967,986 A | 10/1999 | Cimochowski | |
| 5,967,989 A | 10/1999 | Cimochowski et al. | |
| 5,976,994 A | 11/1999 | Nguyen et al. | |
| 5,989,445 A | 11/1999 | Wise et al. | |
| 5,992,769 A | 11/1999 | Wise et al. | |
| 6,015,387 A | 1/2000 | Schwartz et al. | |
| 6,022,756 A | 2/2000 | Sparks et al. | |
| 6,033,427 A * | 3/2000 | Lee | 606/213 |
| 6,035,714 A | 3/2000 | Yazdi et al. | |
| 6,053,873 A | 4/2000 | Govari et al. | |
| 6,062,461 A | 5/2000 | Sparks et al. | |
| 6,092,530 A | 7/2000 | Weissman et al. | |
| 6,109,113 A | 8/2000 | Chavan et al. | |
| 6,136,212 A | 10/2000 | Mastrangelo et al. | |
| 6,140,144 A | 10/2000 | Najafi et al. | |
| 6,140,740 A | 10/2000 | Porat et al. | |
| 6,159,156 A | 12/2000 | Van Bockel | |
| 6,167,757 B1 | 1/2001 | Yazdi et al. | |
| 6,169,321 B1 | 1/2001 | Nguyen et al. | |
| 6,170,488 B1 | 1/2001 | Spillman, Jr. et al. | |
| 6,171,253 B1 | 1/2001 | Bullister et al. | |
| 6,193,670 B1 * | 2/2001 | Van Tassel et al. | 600/486 |
| 6,198,965 B1 | 3/2001 | Penner et al. | |
| 6,206,835 B1 | 3/2001 | Spillman, Jr. et al. | |
| 6,231,516 B1 | 5/2001 | Keilman et al. | |
| 6,232,150 B1 | 5/2001 | Lin et al. | |
| 6,237,398 B1 | 5/2001 | Porat et al. | |
| 6,239,724 B1 | 5/2001 | Doron et al. | |
| 6,286,369 B1 | 9/2001 | Yazdi et al. | |
| 6,287,322 B1 * | 9/2001 | Zhu et al. | 606/213 |
| 6,300,632 B1 | 10/2001 | Liu et al. | |
| 6,350,274 B1 * | 2/2002 | Li | 606/213 |
| 6,442,413 B1 | 8/2002 | Silver | |
| 6,477,426 B1 | 11/2002 | Fenn et al. | |
| 6,524,326 B1 * | 2/2003 | Zhu et al. | 606/213 |
| 6,610,096 B2 | 8/2003 | MacDonald | |
| 6,733,515 B1 * | 5/2004 | Edwards et al. | 606/214 |
| 6,790,220 B2 * | 9/2004 | Morris et al. | 606/213 |
| 6,855,115 B2 * | 2/2005 | Fonseca et al. | 600/488 |
| 6,890,342 B2 * | 5/2005 | Zhu et al. | 606/213 |
| 6,964,675 B2 * | 11/2005 | Zhu et al. | 606/213 |
| 7,147,604 B1 * | 12/2006 | Allen et al. | 600/549 |
| 7,261,733 B1 * | 8/2007 | Brown et al. | 623/1.34 |
| 7,316,704 B2 | 1/2008 | Bagaoisan et al. | 606/213 |
| 7,399,313 B2 * | 7/2008 | Brown et al. | 623/1.13 |
| 7,481,771 B2 * | 1/2009 | Fonseca et al. | 600/486 |
| 7,553,319 B2 * | 6/2009 | Bagaoisan et al. | 606/214 |
| 7,780,699 B2 * | 8/2010 | Zhu et al. | 606/213 |
| 2002/0045921 A1 | 4/2002 | Wolinsky et al. | |
| 2003/0004562 A1 | 1/2003 | DiCarlo | |
| 2003/0229388 A1 | 12/2003 | Hayashi | |
| 2005/0015014 A1 * | 1/2005 | Fonseca et al. | 600/488 |

FOREIGN PATENT DOCUMENTS

| | | |
|---|---|---|
| EP | 0 897 690 A1 | 2/1999 |
| WO | WO 83/03348 | 10/1983 |
| WO | WO 98/29030 | 7/1998 |
| WO | WO 99/26530 | 6/1999 |
| WO | WO 99/42039 | 8/1999 |
| WO | WO 00/32092 | 6/2000 |
| WO | WO 01/36014 | 5/2001 |

* cited by examiner

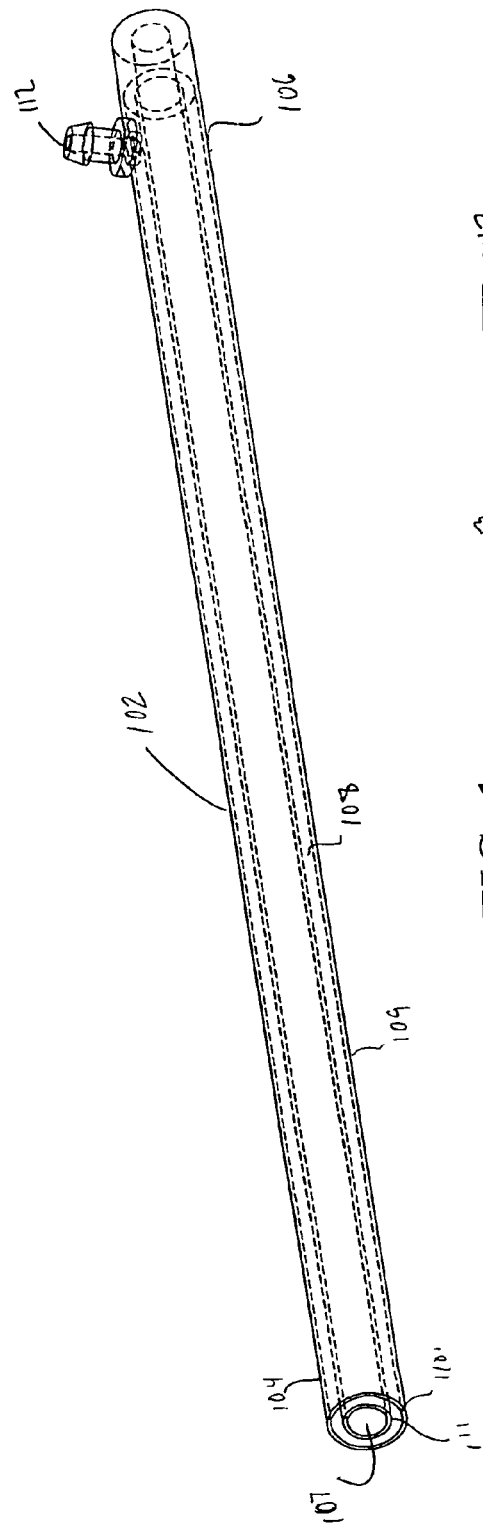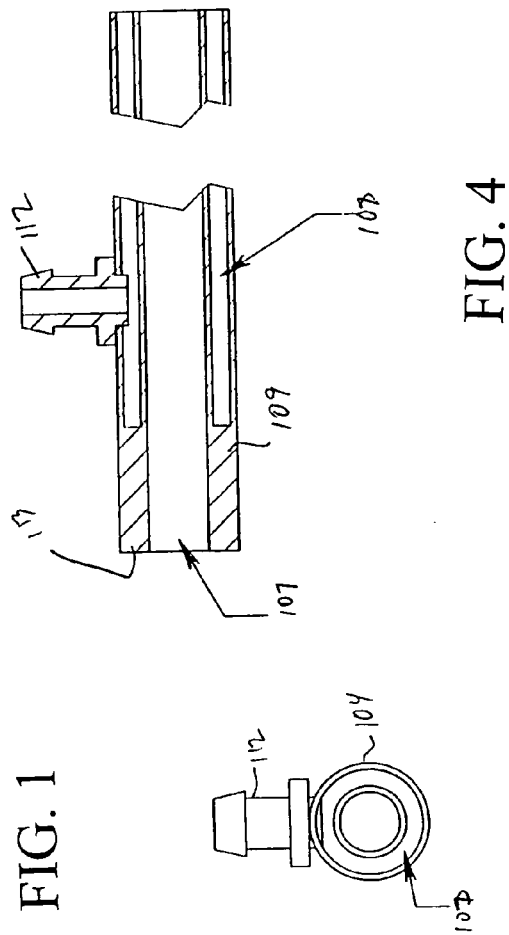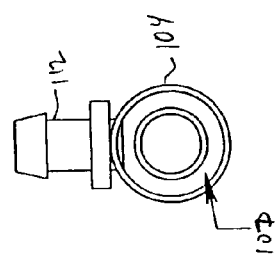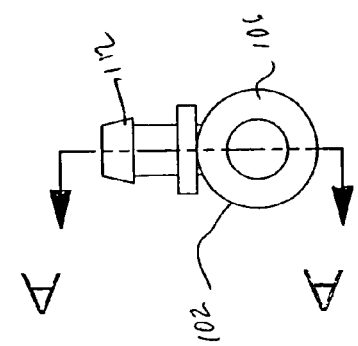

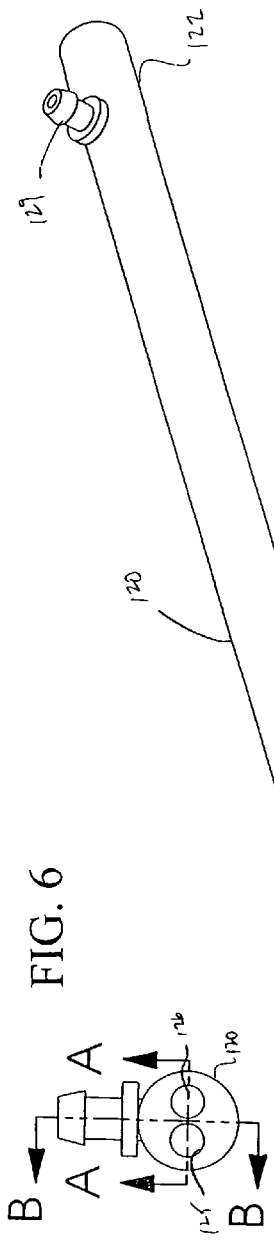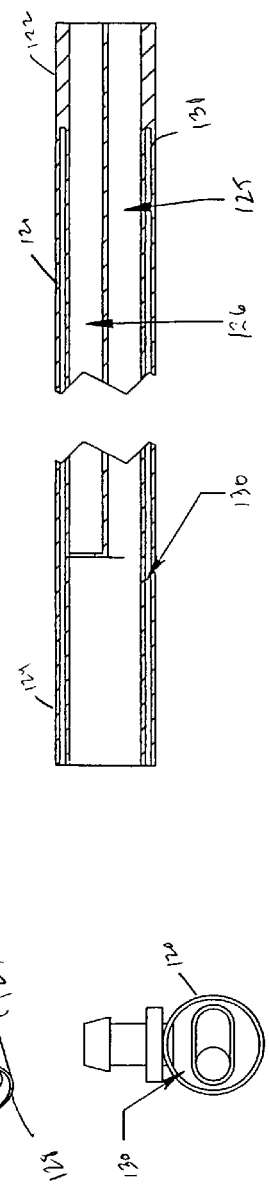
FIG. 5
FIG. 6
FIG. 7
FIG. 8
FIG. 9

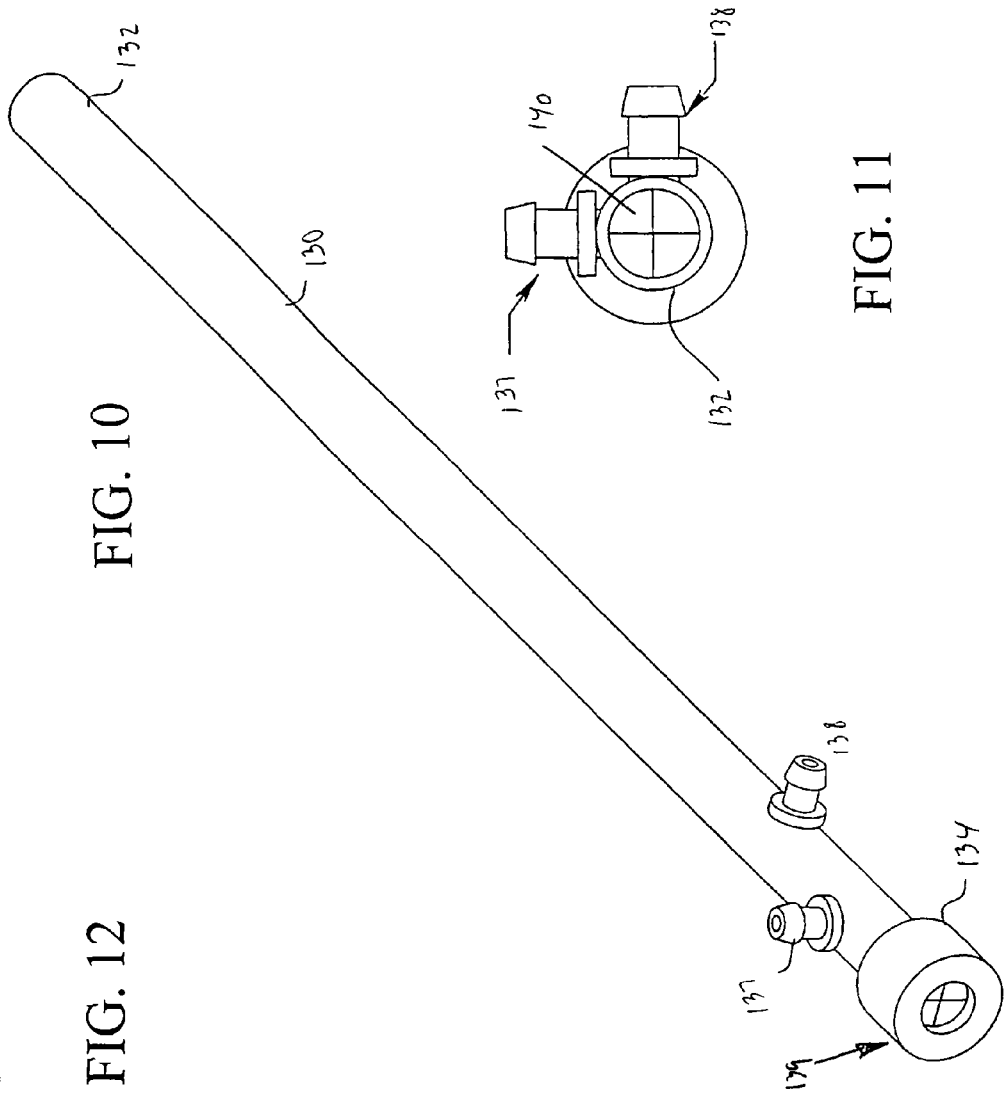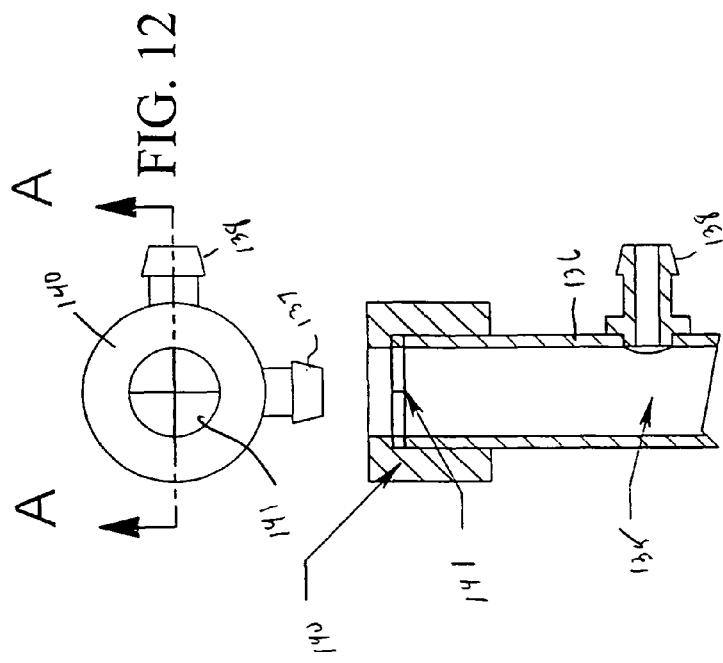

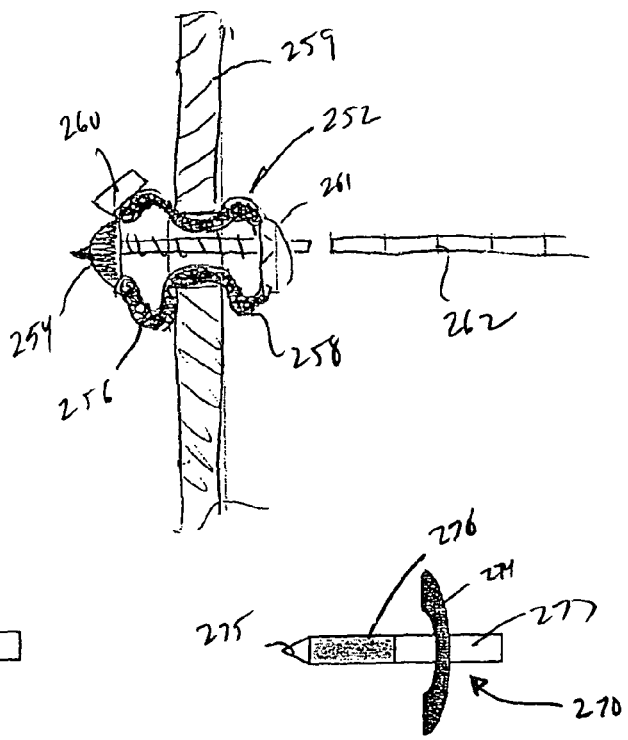
FIG. 55
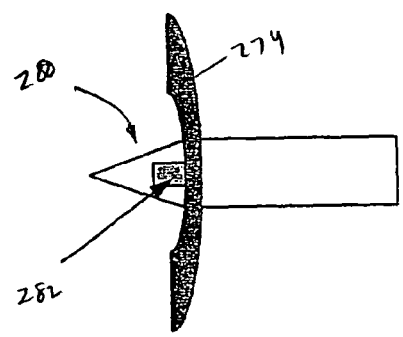
FIG. 56
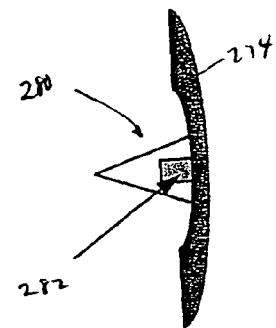
FIG. 57
FIG. 58
FIG. 59

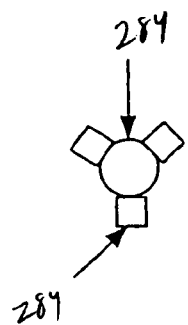
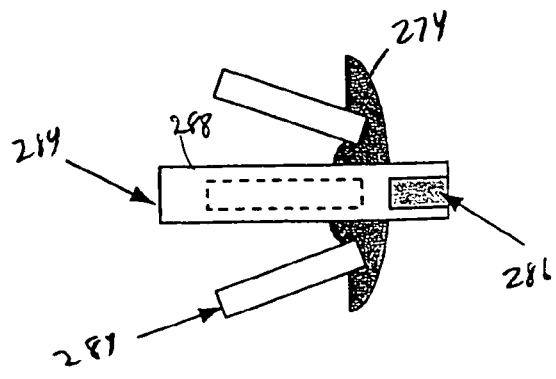
FIG. 60　　　　　　　　FIG. 61
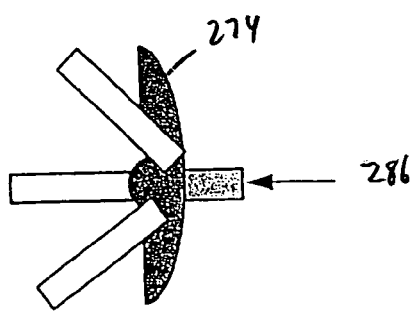
FIG. 62

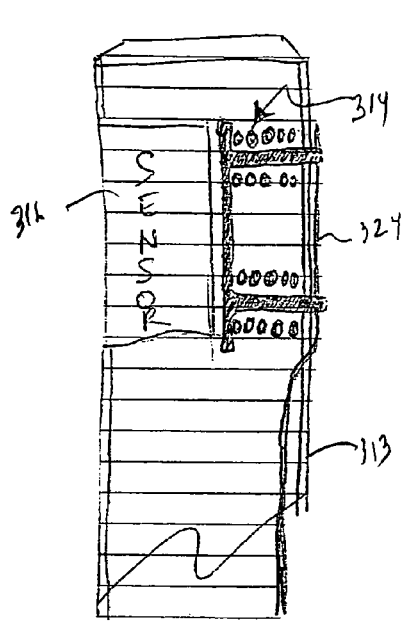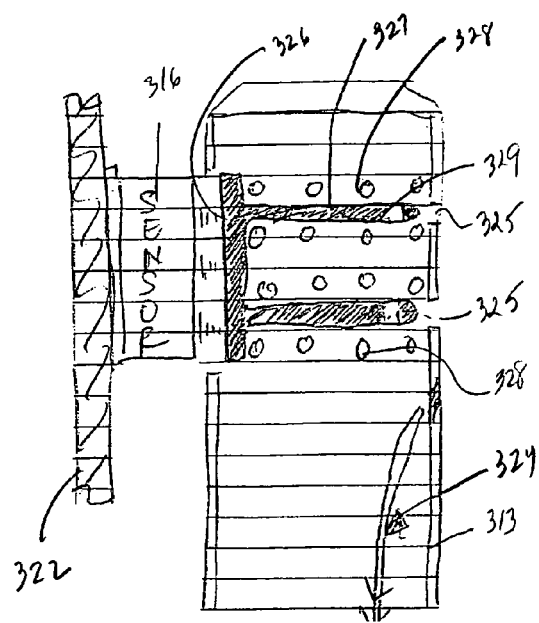
FIG. 68  FIG. 69
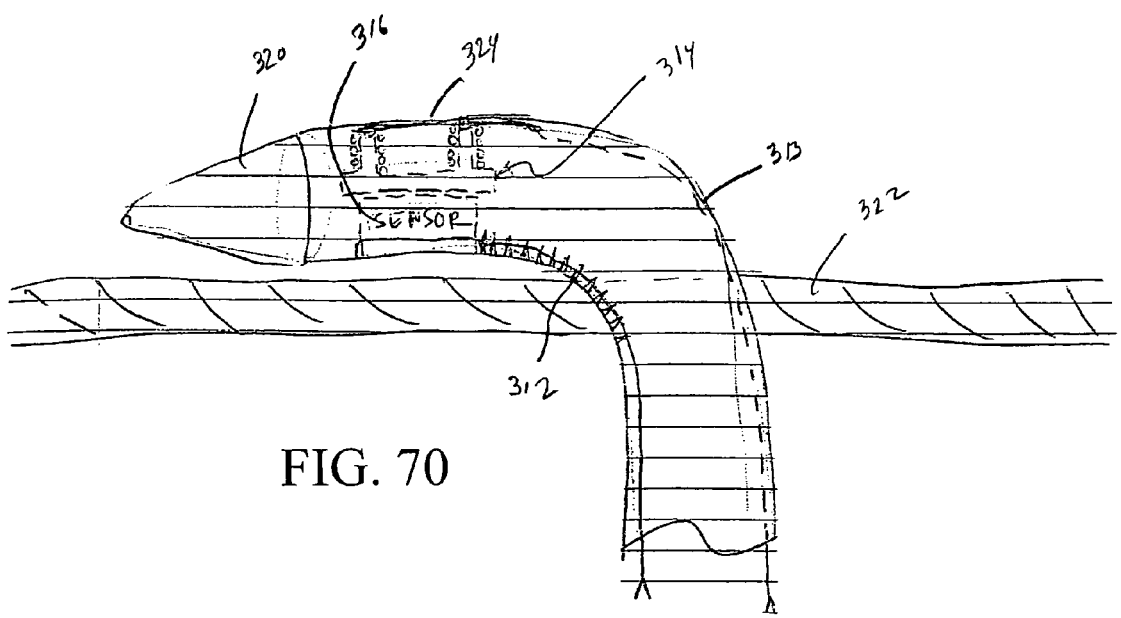
FIG. 70

ANEURYSM SENSING DEVICES AND DELIVERY SYSTEMS

BACKGROUND OF THE INVENTION

1. Field of the Invention
2. General Background and State of the Art

This invention relates to the treatment of body lumens and, more particularly, to the endovascular placement of medical devices within vasculature for the purpose of repairing the same.

Ruptured abdominal aortic aneurysms (AAA) are a leading cause of death in the United States. Treatment options to repair AAA include conventional open surgery and implantation of an endovascular graft. Conventional open surgical repair of AAA involves major abdominal surgery with associated high rates of morbidity. Endovascular grafts have been developed to endoluminally bypass abdominal aortic aneurysms through minimally invasive surgery. Many patients that are unacceptable surgical risks for open repairs are eligible for endovascular graft implantation. Deployment of transfemoral, endovascular grafts to treat AAA is appealing for many reasons: avoidance of an abdominal incision, lack of aortic cross clamping, the potential for regional anesthesia, and a shortened hospital stay.

Untreated AAA have been shown to continue to expand until rupture, with an associated high mortality rate. Implantation of endovascular grafts have also been associated with high complication rates, including perioperative death, conversion to open repair, the need for further intervention, the need for hemodialysis, a failure to cure the AAA, and wound complications.

The inability to obtain or maintain a secure seal between the vessel wall and the endovascular graft is a complication unique to endovascular aneurysm exclusion. Because the term "leak" has been associated with aneurysm rupture following conventional surgery, the term "endoleak" has been proposed as a more definitive description of this complication. It is believed that persistent endoleaks result in continued aneurysm expansion, which may eventually lead to aneurysm rupture. Aneurysms that have been successfully excluded have shown a tendency towards a reduction in aneurysm diameter. Failure to properly exclude the aneurysm from systemic arterial blood pressure keeps the patient at risk of impending rupture. Endoleaks have been classified according to the source of the leaks. Current classifications of endoleaks include four categories. Type I endoleaks are "perigraft" or "graft-related" leaks that involve a persistent channel of blood flow due to inadequate or ineffective sealing at the ends of the endovascular graft, or between overlapping components of a modular system. Type II endoleaks are retrograde flow into the aneurysm sac from patent lumbar arteries, the inferior mesenteric artery, or other collateral vessels. Type III endoleaks result from fabric tears, graft disconnection, or graft disintegration. Finally, Type IV endoleaks are flow through the graft fabric associated with graft wall porosity or permeability. It has been recognized that preoperative patent side branches are not a good predictor of postoperative endoleaks.

There have been a number of reported cases of aneurysm rupture following implantation of an endovascular graft. Some of the ruptures occurred in patients without a documented endoleak.

A number of studies have focused on measurement of pressure within the aneurysm sac following implantation of an endovascular graft, both in the human patient, an animal model, or an in vitro model. Properly implanted endovascular grafts have been shown to reduce the pressure within the aneurysm sac while an endoleak, with or without detectable blood flow, continues to pressurize the sac at pressures equivalent to the systemic arterial pressure. Animal studies utilizing a predictable rupturing aneurysm model have shown that non-excluded aneurysms will rupture. Thrombosed aneurysm sacs may still receive pressurization from a sealed endoleak and this continued pressurization keeps the aneurysm at risk for rupture.

Current methods of patient follow-up include arteriography, contrast-enhanced spiral computed tomography (CT), duplex ultrasonography, abdominal X-ray, and intravascular ultrasound. All of these methods are costly and involve invasive procedures with associated morbidity that may need to be performed in a hospital. None of the imaging methods are completely successful in detecting endoleaks. Therefore, the potential exists for an endoleak to go undetected until eventual rupture. An increase in aneurysm diameter is detectable, and should be considered an indication of endoleak. To avoid aneurysm rupture an increase in aneurysm diameter must be detected in a timely fashion to identify patients in need of corrective endovascular procedures.

An endovascular graft with the ability to measure pressure within the aneurysm sac and provide feedback to the physician could provide acute confirmation of a procedure and identify those patients with persistent pressurization of their aneurysm, and subsequent risk of rupture. Some physicians are advocating that the follow-up examinations of AAA patients focus on pressure measurements, but that this is not currently clinically feasible. Furthermore, follow-up examinations may be performed in the physician's office as opposed to a hospital. Moreover, clinicians will require method to study the pathology of post-endovascularly treated AAA disease.

Accordingly, there exists a need for a non-invasive measurement of pressure, as well as other pertinent parameters, within the aneurysm sac as a means for confirming the success of a procedure as well as identifying patients at risk for aneurysm rupture after the endovascular graft is implanted.

However, providing devices on an endovascular graft to facilitate the measurement of pertinent parameters poses problems. The measurement device increases bulk, which can significantly affect the delivery profile of the endovascular graft and increase the force necessary to deploy the device, such as jacket or release wire retraction forces. Thus, increased bulk is a significant issue for an endovascular graft. Furthermore, attachment of measurement devices to an endovascular graft may require sutures and the suture knots not only provide increased bulk, but are also potential graft wear points. Additionally, tissue growth around a measuring device attached to an implanted endovascular graft may interfere with its function and inaccurate data may result.

Therefore, what is need are alternative approaches to obtaining information regarding the success of an aneurysm repair procedure such as alternative approaches to gaining access to delivering and implanting sensing devices to the repair site. The present invention addresses these problems and other needs.

INVENTION SUMMARY

Briefly and in general terms, the present invention is directed towards approaches to obtaining information regarding the success of repair and aneurysm or other vascular diseases.

The present invention is also contemplated to be used to sense condition in other areas of the body such as all types of the body's cavities, the heart, intestines, the brain, the eye, body ducts or the like. Sensing devices are contemplated to be deployed in an area of a repair site to gather such information.

In one aspect, an external or extra-vascular approach is taken to access vasculature that has been repaired. In the case of aortic aneurysm repair, for example, a retro-peritoneal approach can be taken. The subject vasculature is then punctured and a sensing device is placed within vasculature at the repair site.

In one particular aspect, a vacuum cannula is provided. The vacuum cannula includes a central lumen and is configured to provide a working area for medical devices. In one embodiment, the cannula includes sealing and flushing structure or devices.

Sensing devices are contemplated to be placed within vasculature either attached or unattached to vessel walls or grafts or other medical devices placed within a patient. When the sensors are unattached to vessel walls or other structures, a cage can be provided to space the sensor from anatomy or medical devices and to protect the sensor. The sensors can also include anchors or other devices for attachment to a vessel wall or a graft for example, as well as substructure for releasably engaging a delivery catheter.

In another aspect, the present invention includes a puncture sealer that is releasably connected to a cannula or other elongate medical device. In one embodiment, the sealer includes structure that engages both internal and external surfaces of vasculature to effectively seal a vessel puncture site.

In other aspects of the present invention, sealing structure is incorporated into a sensing device that is releasable from a delivery cannula. Various subassemblies are contemplated such as a single or dual plug approach. The sensor itself can include a sharp terminal end useful for accomplishing the puncturing of a vessel wall or a graft or other medical device. The sensor can further include mating structure, one component of which is adapted to reside within a vessel and the other to create a seal with the first component external the vessel or the graft device. In yet other approaches, the sensor profile is adjustable in vivo to both implant the sensor within a vessel as well as seal the vessel wall or opening resulting from attaching the sensor to a medical device.

A steerable sensor delivery catheter is also provided. The steerable catheter includes structures for releasing the sensor within vasculature at a location remote from a puncture site. Such a sensor can both be deployed free-floating as well as anchored to a vessel wall or other medical devices. Various modes of sensor deployment are contemplated as are auxiliary structures for anchoring sensors to vessel wall.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view, depicting one embodiment of a vacuum cannula;

FIG. 2 is an end view, depicting an inferior end of the vacuum cannula of FIG. 1;

FIG. 3 is an end view, depicting a superior end of the vacuum cannula of FIG. 1;

FIG. 4 is a cross-sectional view, taken along line A-A of FIG. 2;

FIG. 5 is a perspective view, depicting another embodiment of a vacuum cannula;

FIG. 6 is an end view, depicting an inferior end of the vacuum cannula of FIG. 5;

FIG. 7 is an end view, depicting a superior end of the vacuum cannula of FIG. 5;

FIG. 8 is a cross-sectional view taken along line A-A of FIG. 6;

FIG. 9 is a cross-sectional view taken along line B-B of FIG. 6;

FIG. 10 is a perspective view, depicting a third embodiment of a vacuum cannula;

FIG. 11 is an end view, depicting a superior end of the vacuum cannula of FIG. 10;

FIG. 12 is an end view, depicting an inferior end of the vacuum cannula of FIG. 10;

FIG. 13 is a cross sectional view taken along line A-A of FIG. 12;

FIG. 55 is a cross-sectional view, depicting an alternative embodiment of a delivery system incorporating threaded structures for delivering a sensor at an interventional site;

FIG. 56 is a side-view, depicting a sensor delivery system passed through tissue;

FIG. 57 is a side view, depicting a sensor plug of the system of FIG. 56 implanted at an intervention site;

FIG. 58 is a side view, depicting a sensor delivery system including a detachable tip;

FIG. 59 is a side view, depicting the detachable tip of the system of FIG. 58 implanted at an interventional site;

FIG. 60 is an end view, depicting an access tube configured with a plurality of clamps for use in the implantation of a sensor device;

FIG. 61 is a side view, depicting the use of the access tube to deliver a sensor at an implantation site;

FIG. 62 is a side view, depicting the implanted sensor of FIG. 61;

FIG. 68 is a cross-sectional view, depicting another embodiment of a sensor delivery system including a spring ejector mechanism;

FIG. 69 is a cross-sectional view, depicting the deployment of a sensor using the sensor delivery system of FIG. 68;

FIG. 70 is a cross-sectional view, depicting the sensor delivery system of FIG. 68 in use;

DETAILED DESCRIPTION OF THE PREFERRED EMBODIMENTS

Figure 15:
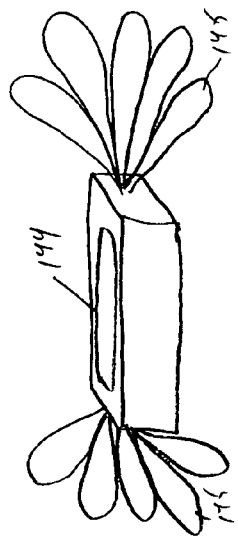
FIG. 15 is a perspective view, depicting the sensor of FIG. 14 with the sensor cage in an expanded configuration.
Figure 14:
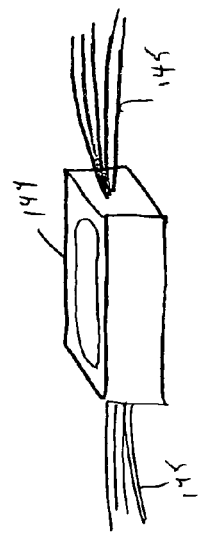
FIG. 14 is a perspective view, depicting a sensor equipped with a first embodiment of a sensor cage in a contracted configuration.
Figure 17:
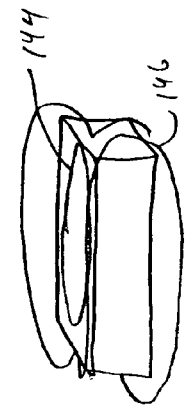
FIG. 17 is a perspective view, depicting the sensor of FIG. 16 with the sensor cage in an expanded configuration.
Figure 16:
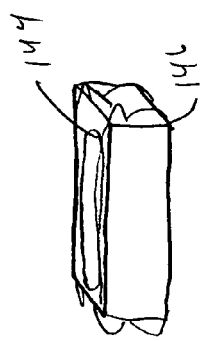
FIG. 16 is a perspective view, depicting a sensor equipped with a second embodiment of a sensor cage in a contracted configuration.
Figure 19:
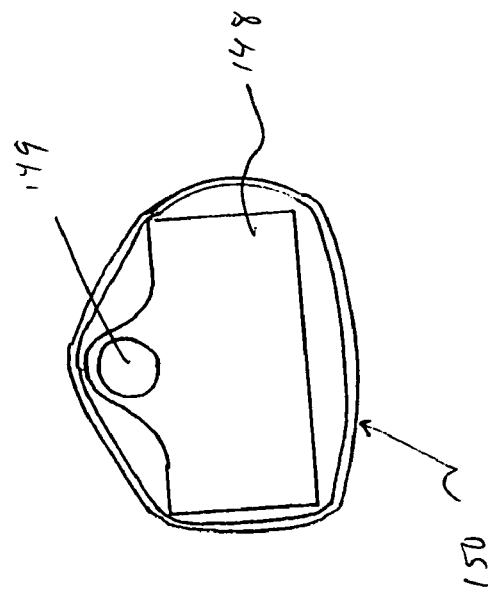
FIG. 19 is an end view, depicting the sensor of FIG. 18 within a delivery cannula.
Figure 18:
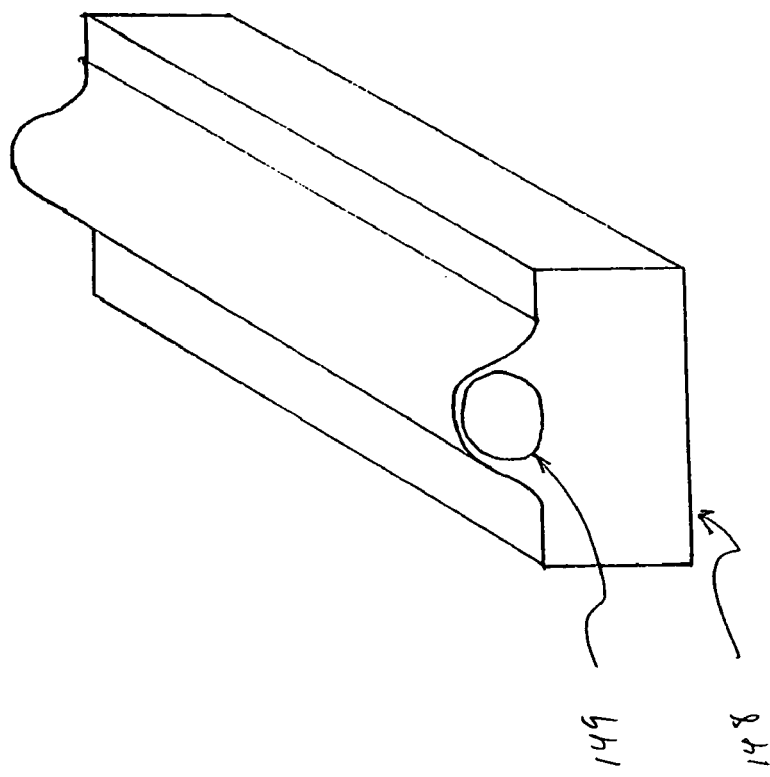
FIG. 18 is a perspective view, depicting a sensor having a guidewire guide.

While the specification describes particular embodiments of the present invention, those of ordinary skill can devise variations of the present invention without departing from the inventive concept.

Referring now to the drawings which are provided for illustration and not by way of limitations, a vacuum cannula 102 is shown in FIGS. 1-4. As for each of the devices disclosed herein, the vacuum cannula 102 is intended to be used in medical procedures and can be utilized in any area of a patient's body. In one particular aspect, the vacuum cannula is designed to be employed to provide a working space on the exterior of any organ or lumen such as a blood vessel. The cannula can also be employed to provide a working space on other structures such as medical devices or grafts. In a situation where it is desirable to gain access to an aorta, for example, a conventional retro-peritoneal approach is taken. A trocar or other introducer device is advanced through the patient's tissue to provide a channel to an interventional or implantation site.

As best shown in FIG. 1, the vacuum cannula 102 is tubular and elongate in configuration. A superior end portion 104 is designed to extend to an interventional site and an inferior end portion 106 is contemplated to remain exterior a patient's body. An internal lumen 107 extends the length of the elongate body. An annular space 108 formed in a tubular wall 109 defining the device extends and substantially the length of the cannula.

The superior end portion 104 can be flexible so that when placed in contact with a body or other surface, an exterior wall 110 of the cannula 102 flares outwardly with respect to an interior wall 111, thus producing an enlarged footprint. The inferior end portion 106 of the cannula is equipped with a valve 112 extending from a side wall 109 of the cannula 102 and providing fluid communication with the annular space 108 defined by inner and outer walls 111, 110. As most clearly seen in FIG. 4, the annular space 108 begins in an area proximate the valve 112 and extends in a superior direction to the superior end portion 104. A terminal end 113 of the inferior end portion 106 does not embody the annular space 108 so that a vacuum can be drawn therethrough via the valve 112 and an auxiliary pump or vacuum (not shown). The internal lumen 107 is thereby left to provide a channel for receiving medical or other instruments to be used at the working space created by the superior end portion 104.

It is to be recognized that while equipping the superior end portion 104 of the cannula 102 with the flexible walls 110 allows for the format of an enlarged footprint, the same also facilitates improving a sealing engagement at a working site by compensating for curvature or other irregularity in the subject surface. Thus, the internal lumen 107 is not subject to the vacuum being drawn through the annular space 108 and the working site is isolated from the suction force.

In an alternate embodiment, it may be contemplated that a cannula can be equipped with a separate additional lumen for receiving a scope should it prove necessary to not use an internal lumen for the advancement of such devices. With reference to FIGS. 5-9, there is shown a tubular and elongate cannula 120 having an inferior end portion 122 and a superior end portion 124 and including a first lumen 125 and a second lumen 126. The first lumen 125 extends a length of the cannula 120, whereas the second lumen 126 extends from the inferior end portion 122 to a point 127 proximal a superior terminal end 128 of the cannula 120. It is also contemplated that the second lumen could extend a length of the cannula.

In this embodiment, the cannula 120 also includes a valve 129 which is in fluid communication with an annular recess 130 formed in an outer wall 131 of the cannula 120. The cannula 120 therefore includes structure for receiving a second medical device in the second lumen 126 which can be maintained separate from other devices passed through the first lumen 125. The cannula also includes a superior terminal end 128 configured to provide a sealable work space when placed in opposition with a target surface. Again, a vacuum can be applied by an auxiliary device via a connection to the valve 129 to aid in the sealing engagement with target tissue and thereby isolate the work space from the environment.

Yet another embodiment of a cannula is shown in FIGS. 10-13. As best seen in FIG. 10, an elongate and tubular sealing cannula 130 can include a superior end portion 132 and an inferior end portion 134. A central lumen 135 is defined by tubular walls 136. First 137 and second 138 valves project from an exterior surface of the tubular wall 136 near the proximal end portion 132. One of the first and second valves 137, 138 can be configured to be connected to a vacuum source whereas the other of the valves can be employed for flushing the lumen 135, or the functions of the valves can be interchangeable.

The proximal end portion 134 of the cannula 130 is further equipped with a seal assembly 139 including a collar 140 and a sealing membrane 141. The seal assembly 139 operates to facilitate the control of a working site such as by controlling blood loss through the cannula and around a puncture or incision in tissue.

As stated, the described cannulas can be employed in any relevant procedure to provide a working site. One such procedure can involve gaining access to a blood vessel such as the aorta. In one particular aspect, it may be desirable to monitor the condition of such a blood vessel or other organ. To do so, a sensor could be placed in the area to be monitored using the cannulas. Such a sensor could measure any relevant parameter such as flow, pressure, oxygen levels or other chemical levels or substances.

Turning now to FIGS. 14-17, there are shown two embodiments of sensors incorporating structures helping to maintain positioning. In one embodiment (FIGS. 14 and 15), the sensor 144 has one or a plurality of hydrophilic ribbons 145 attached to exterior surfaces (such as the ends) thereof. In one aspect, the ribbons 145 absorb water from an environment into which it is placed. Thus, prior to deployment, the ribbons 142 add little bulk to the sensor 144 so that the device can be implanted in an aneurismal sac, for example. After absorbing water from the sac, the ribbon expands from thread-like members into fingers that facilitate limiting movement of the sensor. Such fingers are designed to be atraumatic to a patient's anatomy and are configured to protect the sensor from the anatomy such as from points of calcification.

In another embodiment (FIGS. 16 and 17), a sensor 144 can be equipped with a nitinol wire or ribbon cage 146. The cage 146 can be attached to an external surface of the sensor 144 such as at ends thereof. During advancement and deployment of the sensor within a patient's body or vasculature, the cage 146 is held tight against external surfaces of the sensor 146. When being implanted at an interventional or other site, the cage is permitted to expand to its unrestrained configuration. In its unrestrained configuration, the cage 146 both helps to hold the sensor in place at the implantation site and to protect the sensor 144 from the environment into which it is placed.

There may be situations where it is desirable to deliver multiple sensors to an implantation site. It may be necessary to deliver multiple sensors in rapid succession or it may be preferred to provide a single platform for delivering the plurality of sensors. For such a situation, a sensor 148 can be configured with a guidewire ring 149. In one particular embodiment, the guidewire ring 149 can extend the length of the sensor 148 forming a type of spine longitudinally along the sensor 148. The sensor 141 could also be adapted to include a single or a plurality of spaced individual rings for receiving a guidewire. A pusher or similar structure would then be employed to advance the sensor along the guidewire to an implantation point.

To minimize the size of the assembly for delivering the sensor 148 with a guidewire ring 149, the cannula 150 can be shaped to protect the sensor 149. That is, the cannula 150 can be irregularly shaped in cross-section. It is contemplated that this irregular shape can be advantageous in assisting in supporting the sensor 148 as it is advanced through the cannula 150, thereby providing an easier pathway to the implantation or release site.

Various methods and approaches for deploying sensors like those described above and other sensors and medical devices will be described below. The sealing cannulas previously presented can be employed as necessary to provide a working space.

In the situation where it is decided that a sensor is needed in an aneurismal sac that has been excluded or repaired by a graft device for example, an approach and apparatus is required for deploying a micro-sensor (or other system) that measures important parameters providing information regarding the status of the repaired section of vasculature. Ultrasound visualization can first be utilized to study the area of the aneurismal sac into which the sensor is to be placed.

Next, laparoscopic access can be relied upon to approach the aneurysm. From the flank of the patient (preferably the left side) approximately at a midpoint between the costal margin and iliac crest, a 2 cm incision is made. A dissection is made through the muscle layer into the pre-peritoneal space. A one liter balloon can be placed in the dissected area and be inflated until the patient's kidney is clearly visible through the balloon. After removing the balloon, a 10 mm trocar is inserted and the area is insufflated. A second incision the size of 1 cm is made into the cavity now formed into which is placed a 5 mm trocar to be used for a visualization scope.

Access for surgical tools to the area is provided by the 10 mm trocar. The dissection of the area is continued toward the patient's spine within the pre-peritoneum until the aneurysm sac is reached. The region of the aneurysm wall where the sensor is to be delivered is also dissected.

In one particular approach, a purse string (not shown) is sewn at the point of entry to the aneurismal sac. Either with the sensor deployment device (see discussion below) itself or through separate means, an incision large enough to accept the deployment device is created in the aneurysm wall within the purse string suture. Using ultrasound visualization, the location of the access point is verified. The sensor can then be deployed within the aneurysm sac. While tensing the purse string sutures, the deployment tube is withdrawn. The purse string suture is then tied off and the area is checked for leaks. Finally, the area is deflated and the external incisions are closed.

Although the above has been described for implanting a sensor into an aneurismal sac, similar approaches can be used to gain access to other organs or areas of a patient's body. Additionally, the described approach is relevant to other devices for inserting sensors within or upon an aneurysm wall with or without the use of sealing cannulas.

Moreover, alternate methods and structures for sealing a puncture or incision made in an aneurysm or other body tissue may be desirable. With reference to FIGS. 20-23, there is shown a telescoping cannula assembly 158 including a longitudinally extendable and retractable wire 159 and a longitudinally extendable and retractable internal tubular cannula 160. In a situation where the cannula assembly 158 was employed to deliver a sensor or other component across a tissue layer 162 (while recognizing that such delivery can be across other layers such as graft material), prior to removing the cannula 158, a terminal end portion 163 of the wire 159 can be configured with a first collapsible umbrella or cup 164. The first cup 164 is collapsible in an inferior direction for ease of advancement through the cannula and includes an interior opened in an inferior direction.

Figure 20:
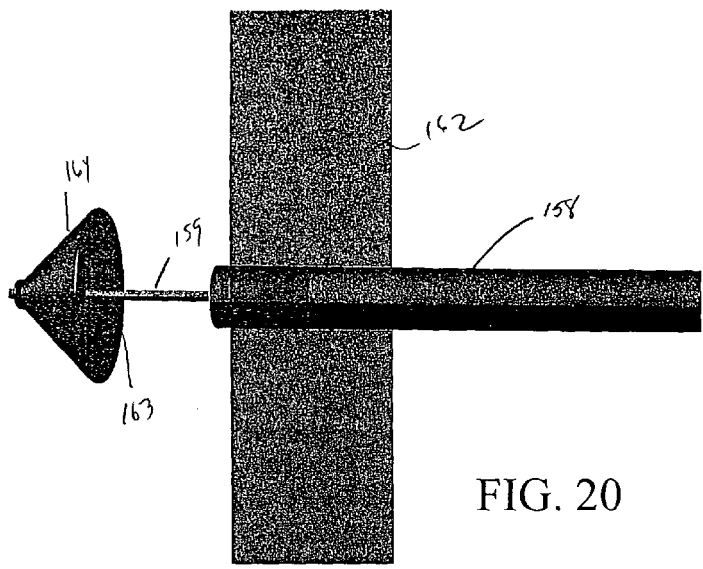
FIG. 20 is a perspective view, depicting a first step in a method of sealing a puncture site.
Figure 21:
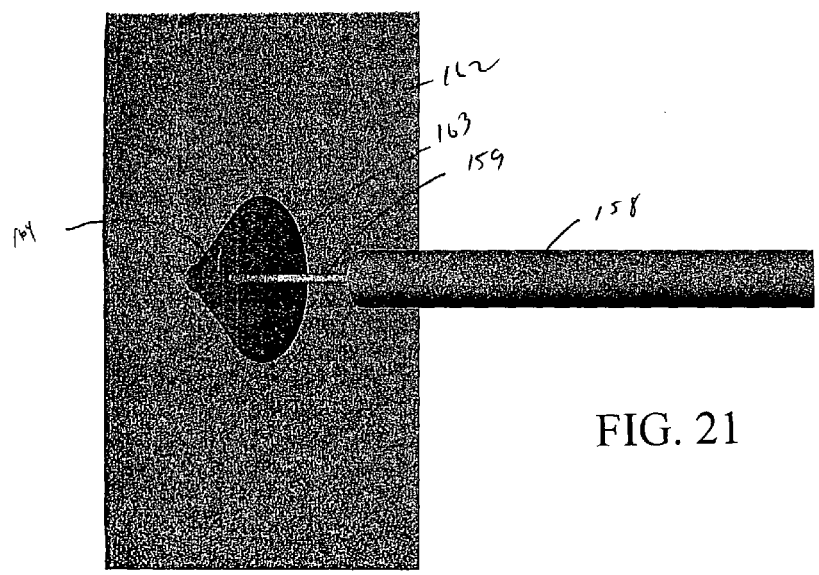
FIG. 21 is a perspective view, depicting a second step in a method of sealing a puncture site.
Figure 22:
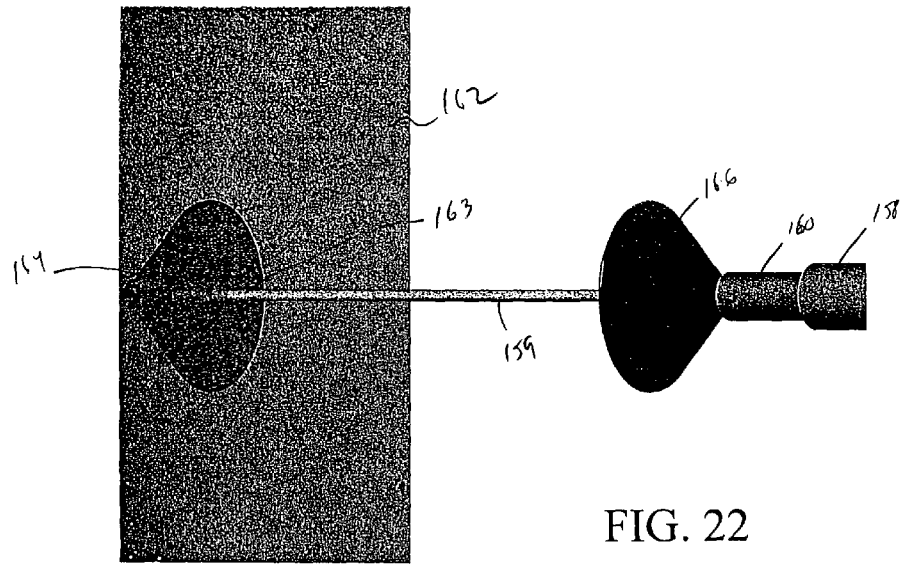
FIG. 22 is a perspective view, depicting a third step in a method of sealing a puncture site.
Figure 23:
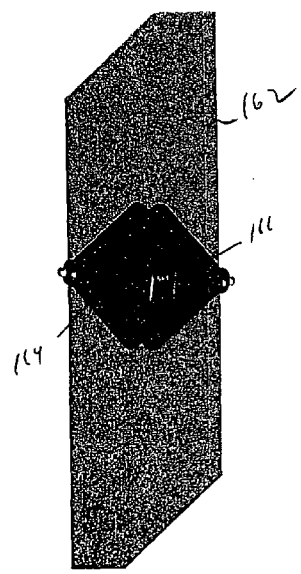
FIG. 23 is a perspective view, depicting a fourth step in a method of sealing a puncture site.
Figure 24:
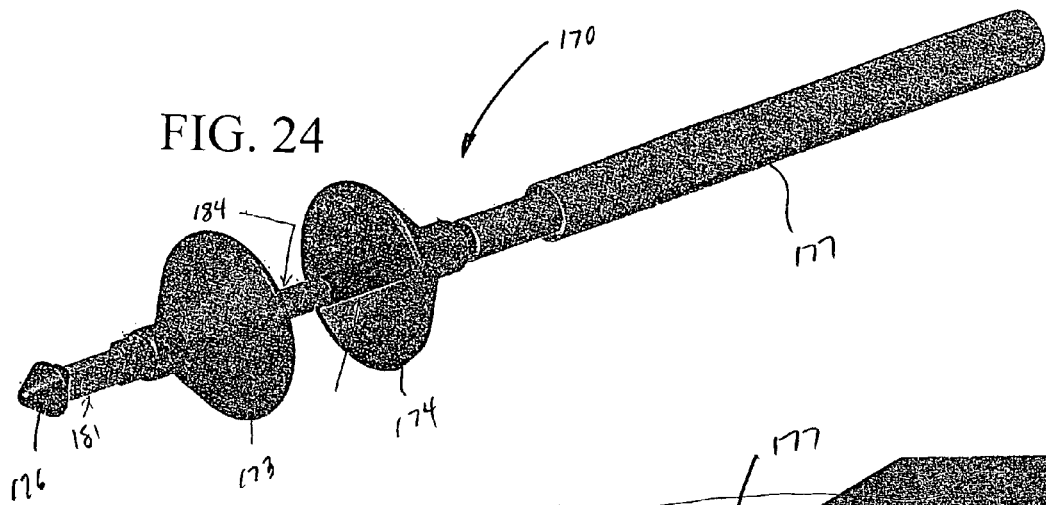
FIG. 24 is a perspective view, depicting a superior end of a sensor delivery and wound puncture system.
Figure 25:
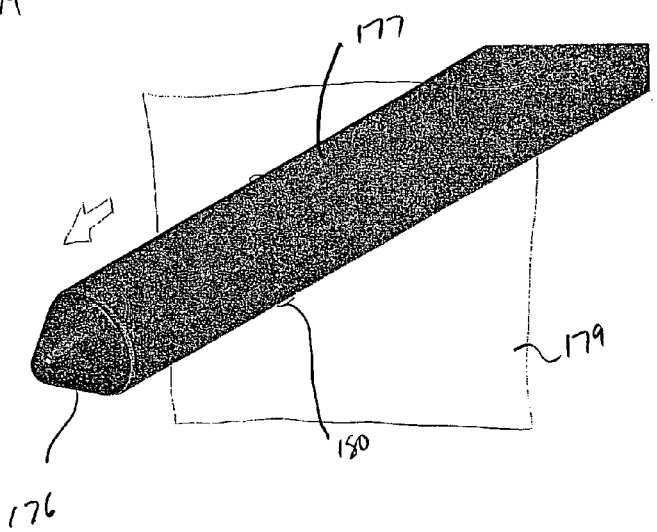
FIG. 25 is a perspective view, depicting a first step of employing the sensor delivery and wound puncture system of FIG. 24.
Figure 26:
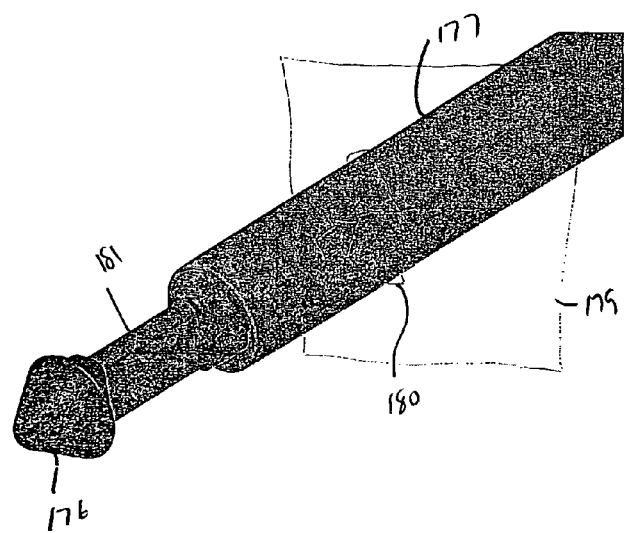
FIG. 26 is a perspective view, depicting a second step involving the sensor delivery and wound puncture system of FIG. 25.
Figure 27:
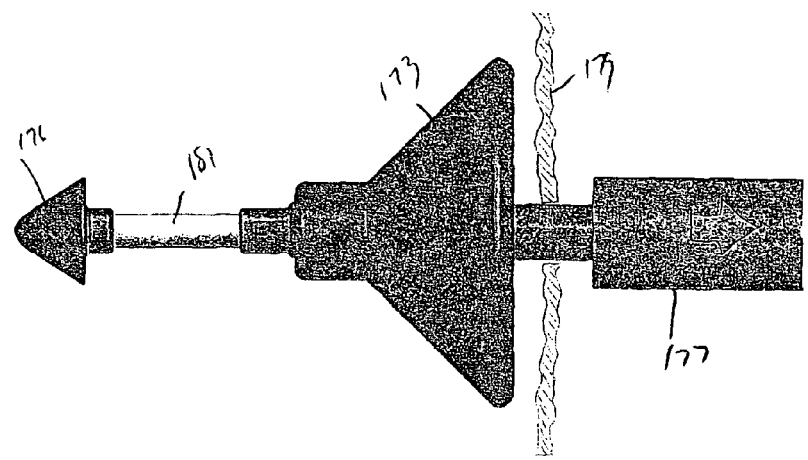
FIG. 27 is a perspective view, depicting a third step involving the sensor delivery and wound puncture system of FIG. 25.

Once placed beyond the tissue (or other) layer 162, the first cup 164 expands to an uncollapsed state (FIG. 20). The wire 159 and cannula assembly 158 are then pulled in an inferior direction placing the first cup 164 in apposition with a far surface of the tissue layer 162. Next, a second umbrella or cup 166 is advance by the internal tubular cannula 160 through the cannula assembly 158. The second cup 166 is also collapsible but is configured to collapse and includes an interior facing in a superior direction.

The second cup 166 is continued to be advanced along the wire 159 until the second cup 166 is placed in apposition with a near side of the tissue layer 162. Threads, notches or ridges (not shown) are provided on the wire for locking the two cups 164, 166 into sealing engagement about the tissue to thereby exclude a puncture or other opening between the cups. Additionally, the wire 159 can be equipped with structure such as threads allowing the disengagement of the first and second cups 164, 166 therefrom. Subsequent to the disengagement of the cups 164, 166 from the wire 159, the cannula assembly 158 can be removed from the area.

Turning now to FIGS. 24-31, there is shown a sensor delivery system 170 including ratcheting structures and flexible plugs 173, 174. The elongate sensor delivery system has a length sufficient to extend from outside a patient's body to target tissue and includes a terminal end 176 having a pointed cone profile that forms or contains therein a sensor adapted to provide information regarding a particular parameter of interest such as pressure or flow or constituency. An outer sheath structure 177 encapsulates various pusher mechanisms, inner shafts and the plugs 173, 174 when the device is assembled prior to use and for advancement to target tissue 179 (See FIG. 25). Again, in other applications, the target can be other structure such as a graft wall or other relevant structure.

In a first step of use, the delivery system 170 is passed through a hole or incision 180 placed within a target tissue 179. Although not shown, a sealed or protected working space can be provided by one of the cannulas described above. Likewise, access to the target tissue can be achieved laparoscopically as also described above. After passing the device through the target tissue 179, the outer sheath structure 177 is withdrawn relative to the terminal end 176 to expose a superior portion of a first inner shaft 181 (See FIG. 26) which can have a generally rectangular profile and can contain a sensing device, etc. Further withdrawal of the sheath 177 reveals that the first shaft 181 connects the terminal end 176 to the first flexible plug 173. Whereas various configurations are acceptable, the first plug 173 is shown as having a generally conical profile with a hollow interior and no base and being configured so its interior faces in an inferior direction.

Figure 28:
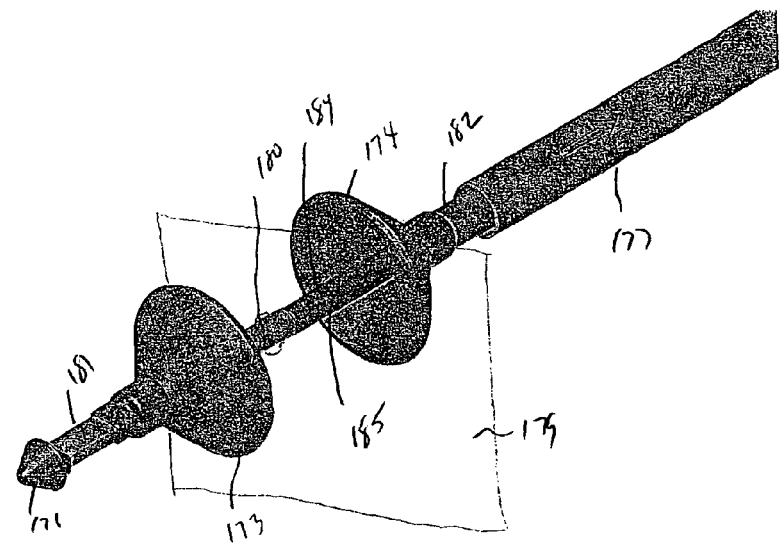
FIG. 28 is a perspective view, depicting a fourth step involving the sensor delivery and wound puncture system of FIG. 25.
Figure 29:
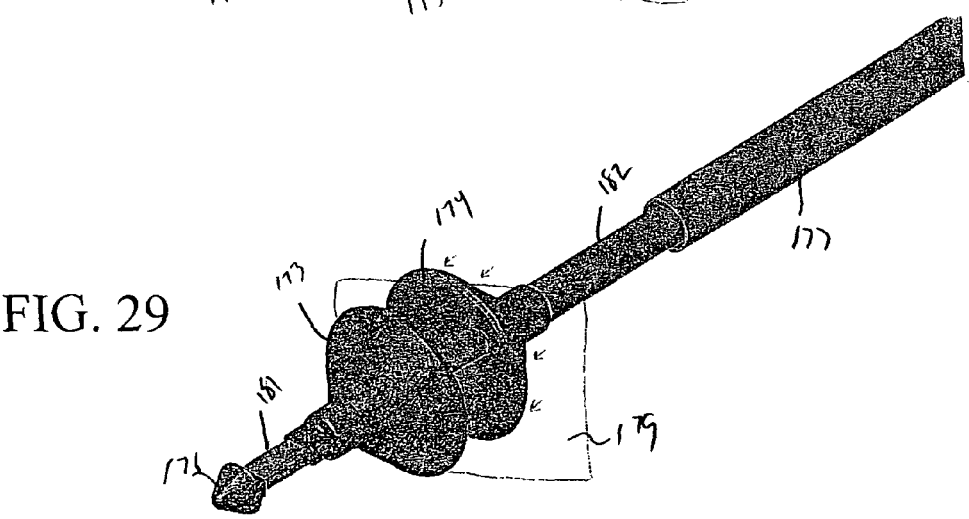
FIG. 29 is a perspective view, depicting a fifth step involving the sensor delivery and wound puncture system of FIG. 25.
Figure 30:
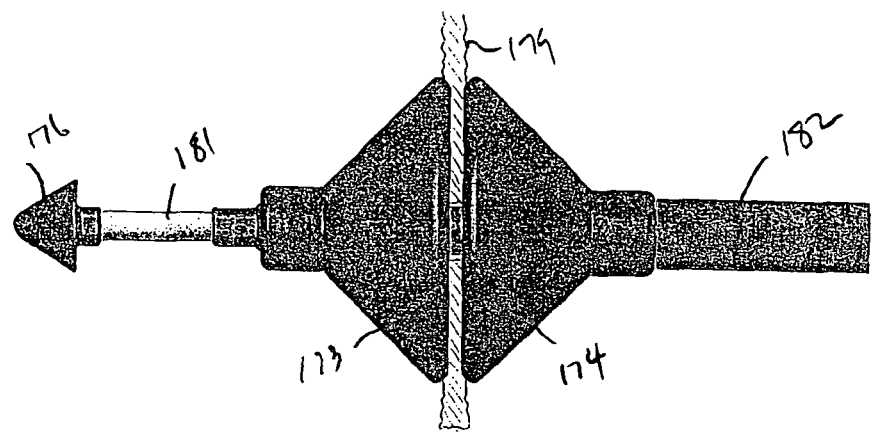
FIG. 30 is a perspective view, depicting a sixth step involving the sensor delivery and wound puncture system of FIG. 25.
Figure 31:
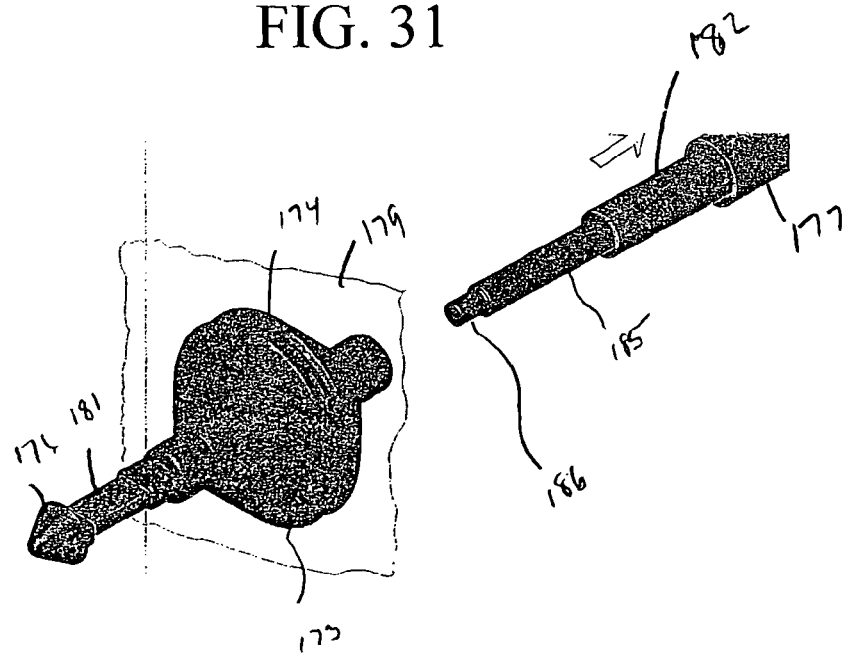
FIG. 31 is a perspective view, depicting a seventh step involving the sensor delivery and wound puncture system of FIG. 25.
Figure 32:
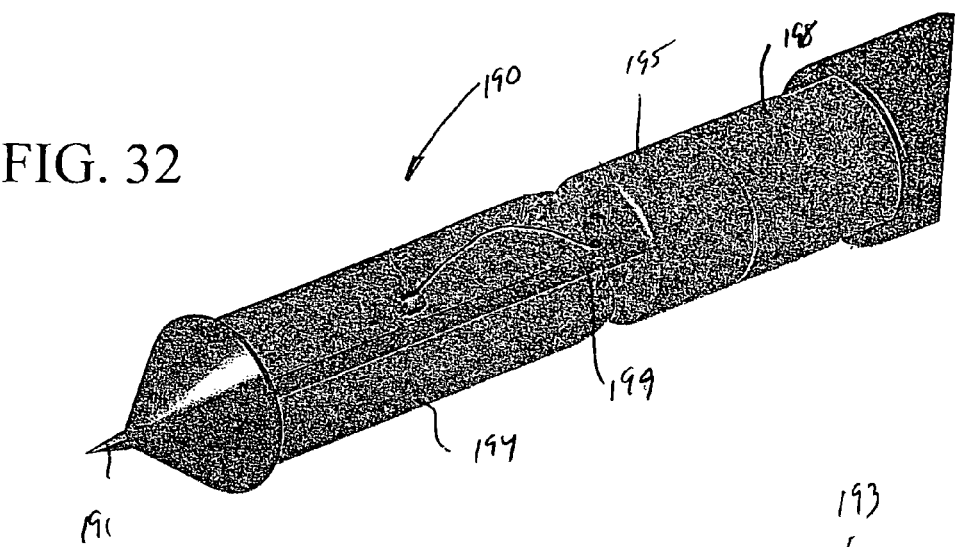
FIG. 32 is a perspective view, depicting a superior end portion of a sensor delivery system.
Figure 33:
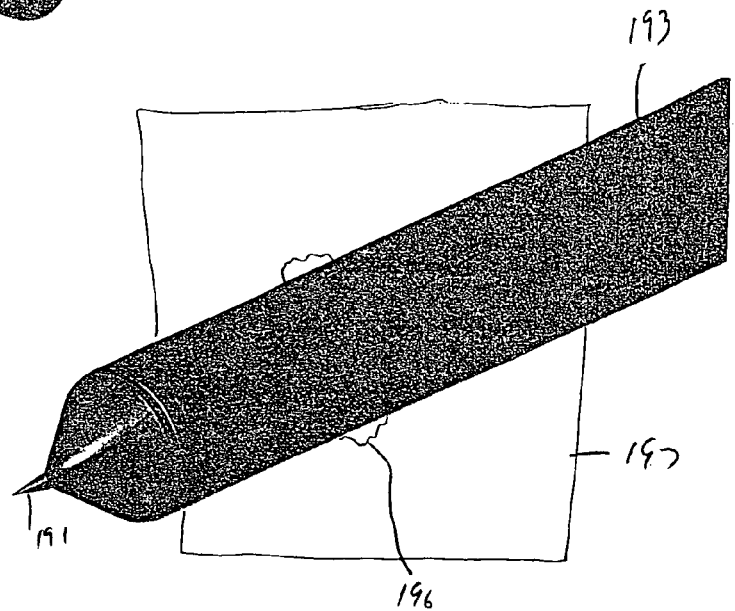
FIG. 33 is a perspective view, depicting a first step of employing the sensor delivery system of FIG. 32.
Figure 34:
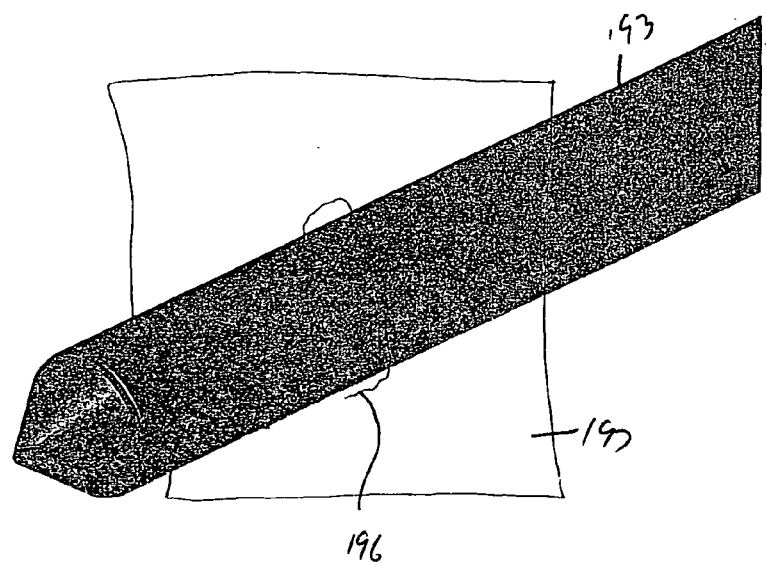
FIG. 34 is a perspective view, depicting a second step of employing the sensor delivery system of FIG. 32.
Figure 35:
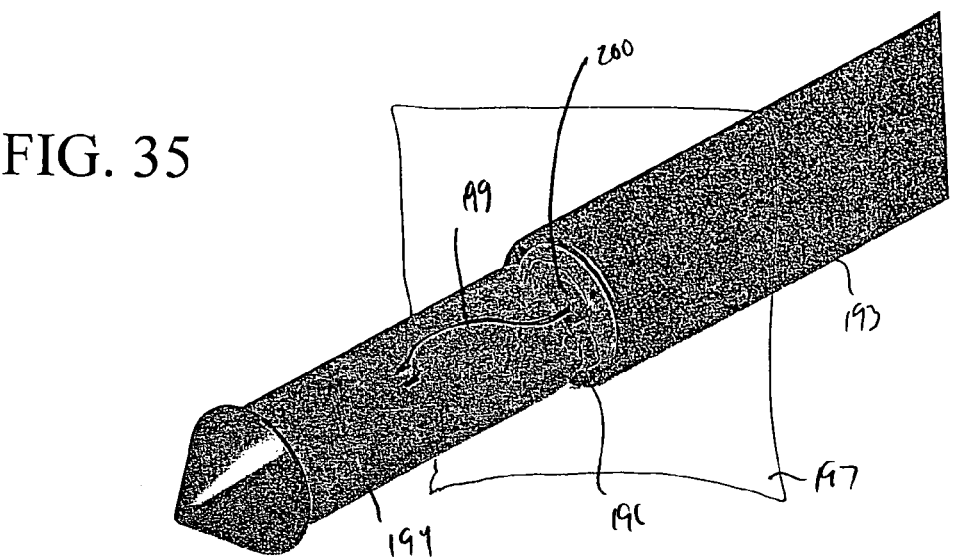
FIG. 35 is a perspective view, depicting a third step of employing the sensor delivery system of FIG. 32.
Figure 36:
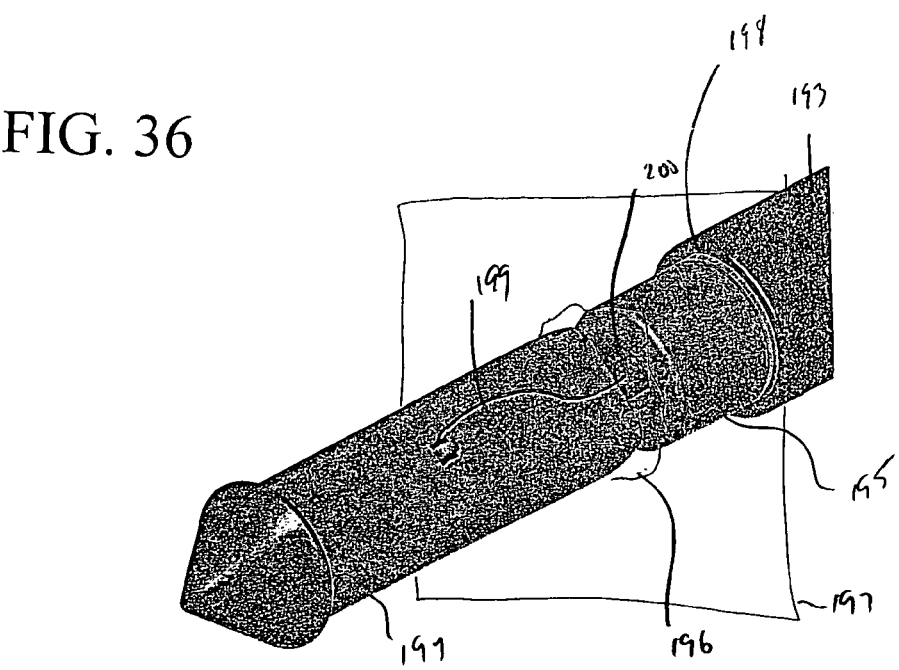
FIG. 36 is a perspective view, depicting a fourth step of employing the sensor delivery system of FIG. 32.
Figure 37:
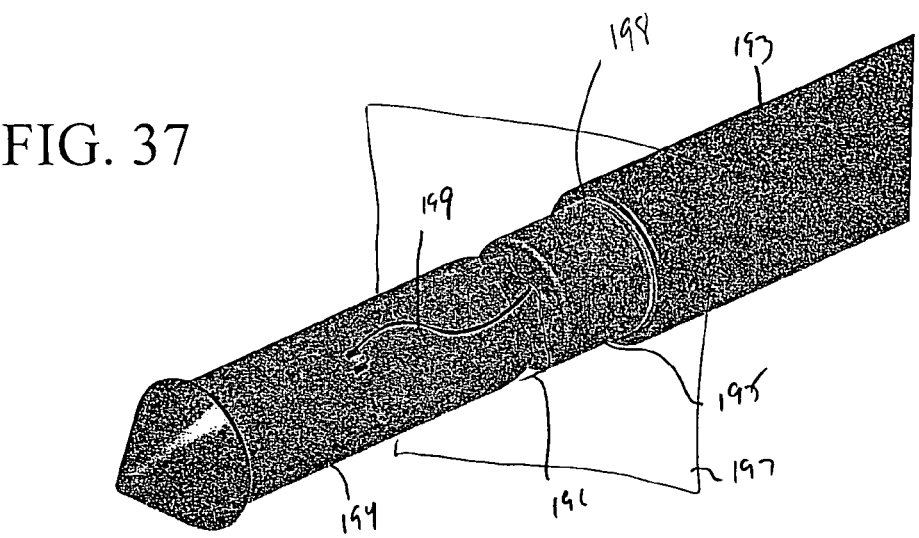
FIG. 37 is a perspective view, depicting a fifth step of employing the sensor delivery system of FIG. 32.

Once the first plug 173 has been deployed beyond the target tissue 179, the outer sheath is withdrawn further to expose and deploy the second plug 174 on an inferior side of the target tissue 179 (FIG. 28). The second plug 174 has a similar profile to that of the first plug 173. Being flexible, each of the first and second plugs assume collapsed forms for advancement to the target tissue and spring open when released from the sheath 177. Next, by advancing an inner pusher device 182, the second plug 174 is advanced along a second inner shaft 184 which is connected at its terminal end to the interior of the first plug 173. The second inner shaft 184 includes a first part of a ratcheting mechanism 185 in the form of teeth or equivalent structure that cooperates with corresponding structure formed on the second plug 174 which forms a second part of a ratcheting mechanism (not shown). Although any conventional ratcheting mechanism is acceptable, such a mechanism must be capable of accomplishing a ratcheting function through the engagement of the pusher 182 against the second plug 174 to thereby advance the second plug 174 into apposition with an inferior side of the target tissue 179.

As the pusher 182 is advanced to place the second plug 174 against the target tissue 179 and the first plug 173 is drawn into apposition with a superior side of the target tissue 179, the hole or incision 180 is sealed within the plugs 173, 174.

A releasable connection 186 in the form of a threaded shaft or spring release mechanism is provided at a terminal end of the second inner shaft 185 and the second plug 174 to permit the disengagement of the second plug from the delivery system 170. The sensor is thereby placed within or beyond the target tissue 179 and held in place by the first shaft 181.

In an alternative approach (See FIGS. 32-38), a sensor delivery system 190 includes an elongate body with a retractable sharp terminal end 191. Again, the sensor delivery system has a length sufficient to extend from exterior a patient's body to a target tissue or medical device placed within the patient's body. A longitudinal retractable and extendable outer sheath 193 provides a cover for a sensor assembly 194 and a ratcheting/sealing mechanism 195 as well as other subcomponents.

In use, the sensor delivery system 190 can be placed through a hole or incision 196 in target tissue or other structure 197, or the sharp retractable tip 191 can be used to create the hole or structure 196. Again, a sealed working site can be provided by the above-described cannula apparatus. After placing the superior end portion of the sensor delivery system 190 beyond the target tissue 197, the sharpened tip 191 can be retracted (See FIG. 34). Next, the outer sheath 193 is withdrawn while holding the superior end portion stationary to reveal the sensor assembly 194 and ratcheting/sealing mechanism 195 as well as an inner pusher member 198 and a pusher wire 199.

Figure 38:
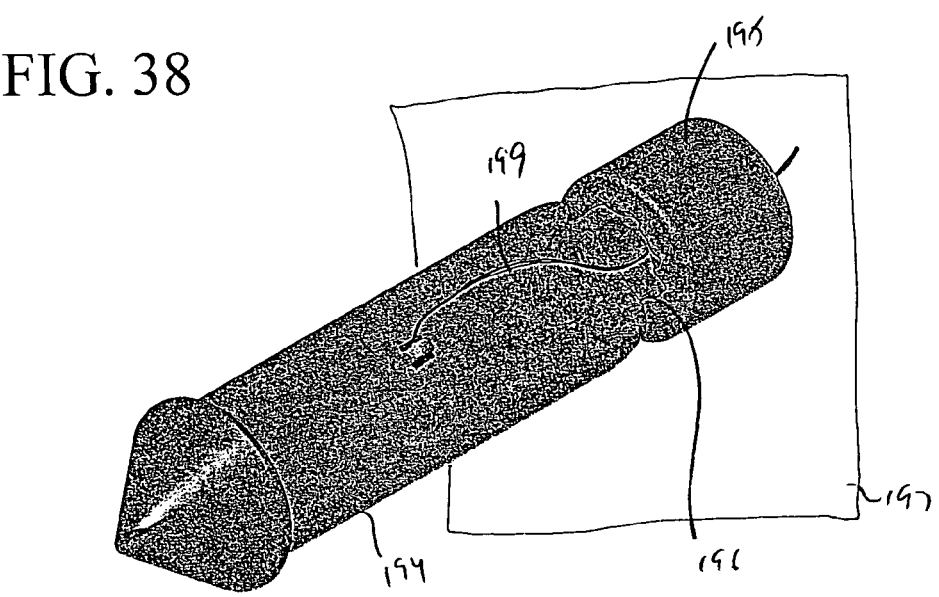
FIG. 38 is a perspective view, depicting a sixth step of employing the sensor delivery system of FIG. 32.
Figure 38A:
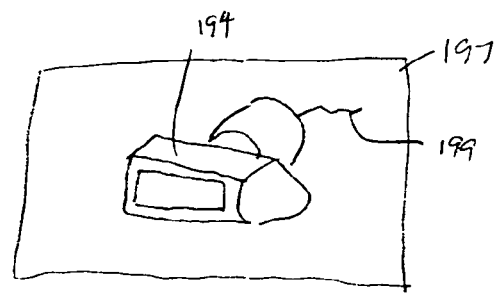
FIG. 38A is a perspective view, depicting a seventh step of employing the sensor delivery system of FIG. 32.
Figure 39:
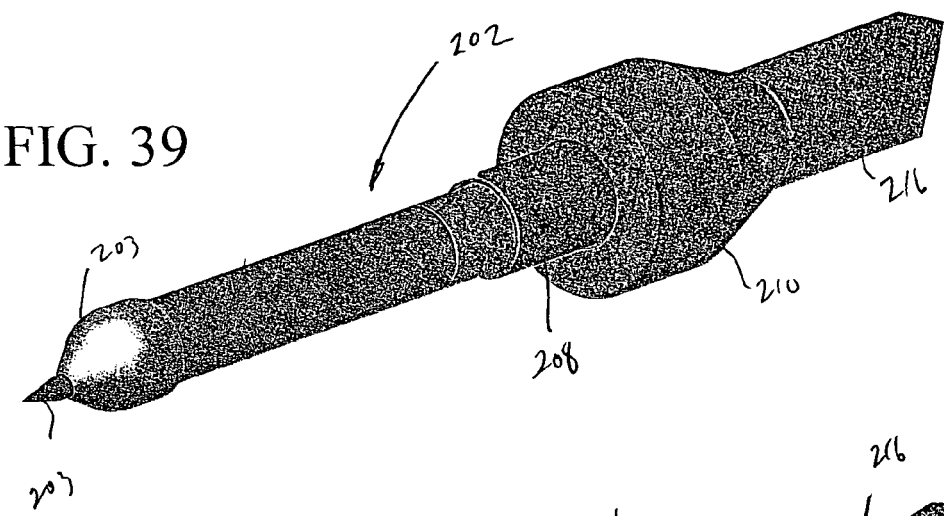
FIG. 39 is a perspective view, depicting a superior end portion of another embodiment of a sensor delivery system.
Figure 40:
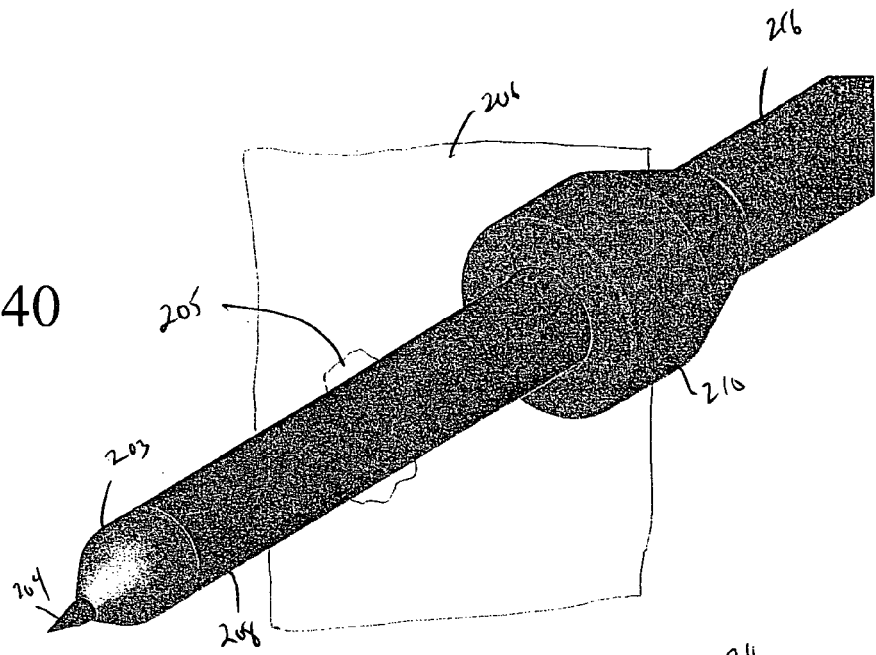
FIG. 40 is a perspective view, depicting a first step of employing its sensor delivery system of FIG. 39.
Figure 41:
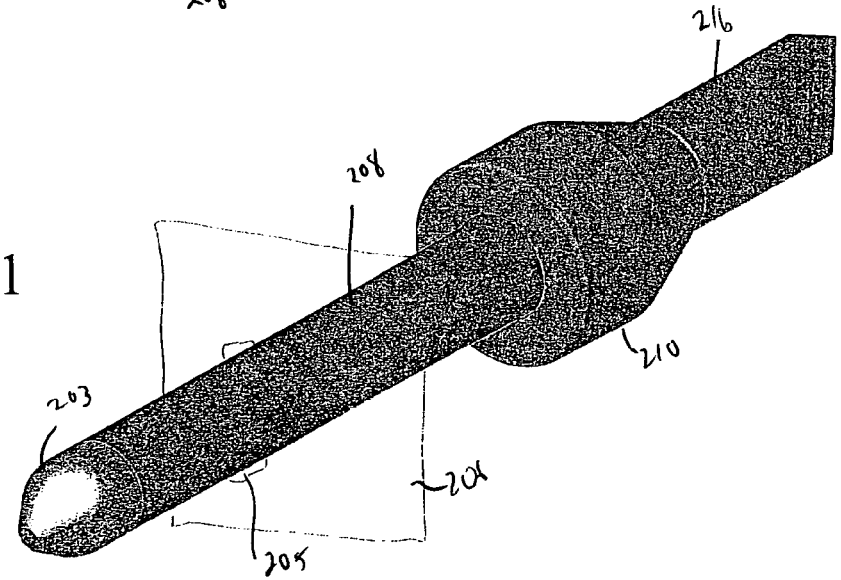
FIG. 41 is a perspective view, depicting a second step of employing its sensor delivery system of FIG. 39.

The pusher wire 199 is attached to an exterior of the sensor assembly 194 opposite its sensing membrane (not shown) and is isolated from the ratcheting/sealing mechanism 195 by an inner tubular member 200. The push wire 199 functions to link the sensor assembly 194 to the ratcheting/sealing membrane 198 as well as to position an inferior end of the sensor 194 in apposition with a far side of the target tissue 197 (See FIG. 36). The inner tubular member 200 is then withdrawn (FIG. 37) to permit the ratcheting/sealing member 195 to be advanced against the near side of the target tissue 197 by the pusher member 198. The mating area of the ratcheting/sealing member 195 is contemplated to be made from sealing promoting materials. The pusher wire 199 is then cut leaving the sensor assembly 194 in a position to gather the desire data. (See FIG. 38A)

Figure 42:
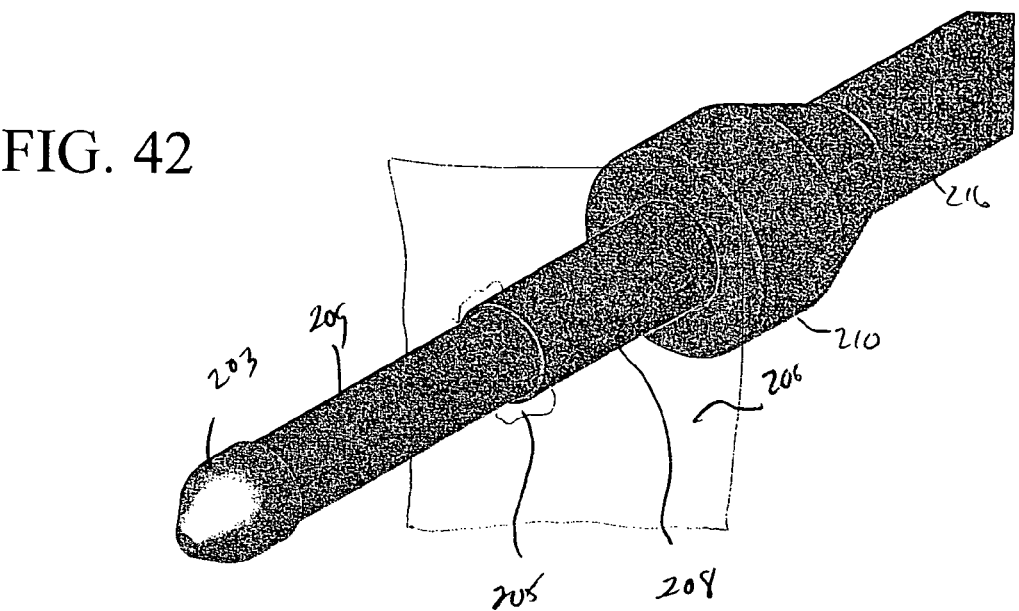
FIG. 42 is a perspective view, depicting a third step of employing its sensor delivery system of FIG. 39.
Figure 43:
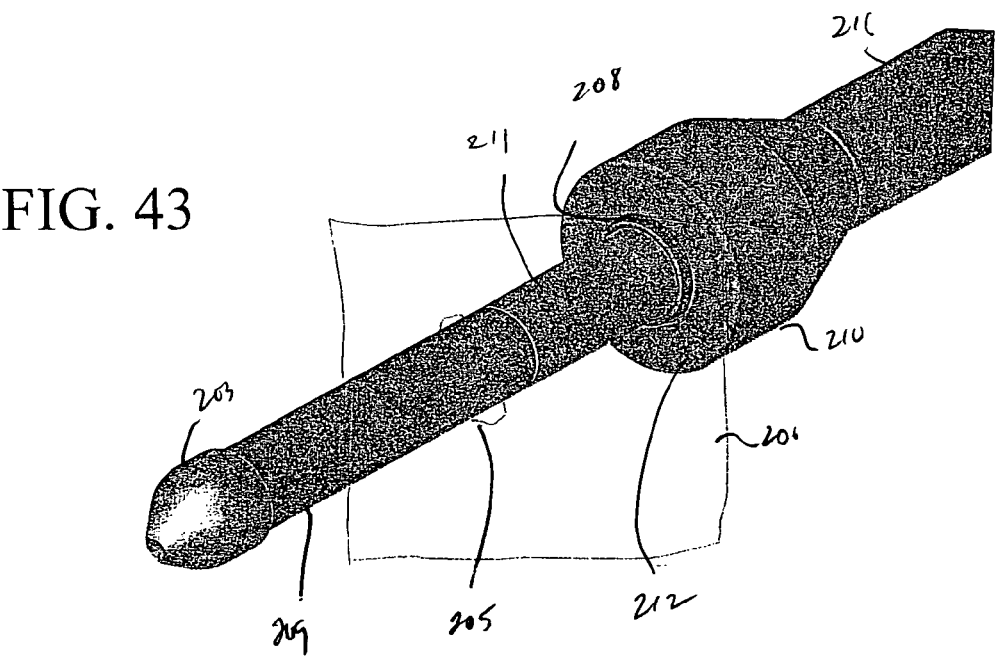
FIG. 43 is a perspective view, depicting a fourth step of employing its sensor delivery system of FIG. 39.
Figure 44:
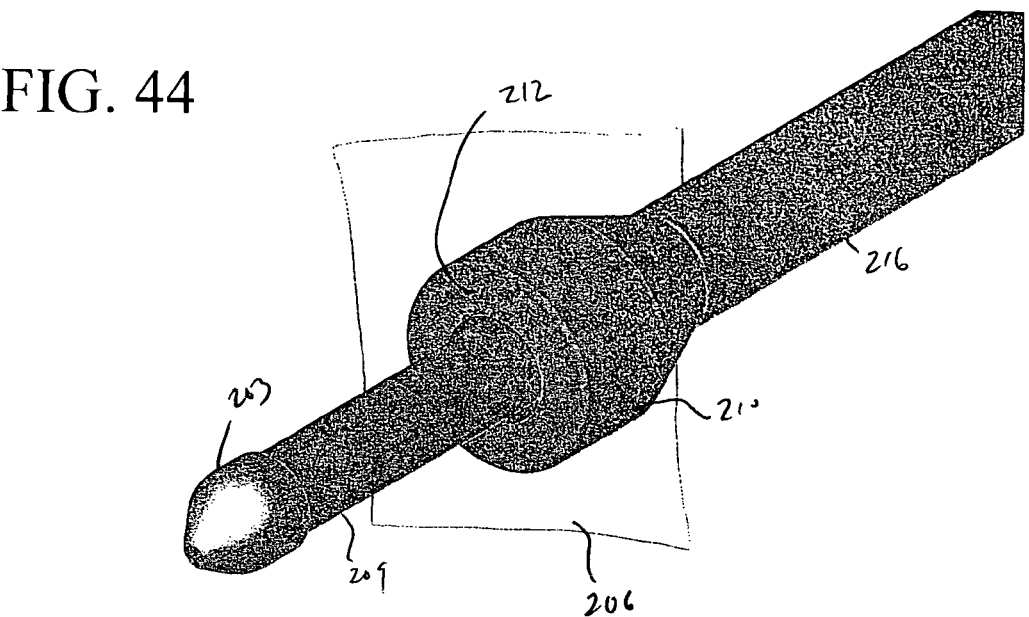
FIG. 44 is a perspective view, depicting a fifth step of employing its sensor delivery system of FIG. 39.
Figure 45:
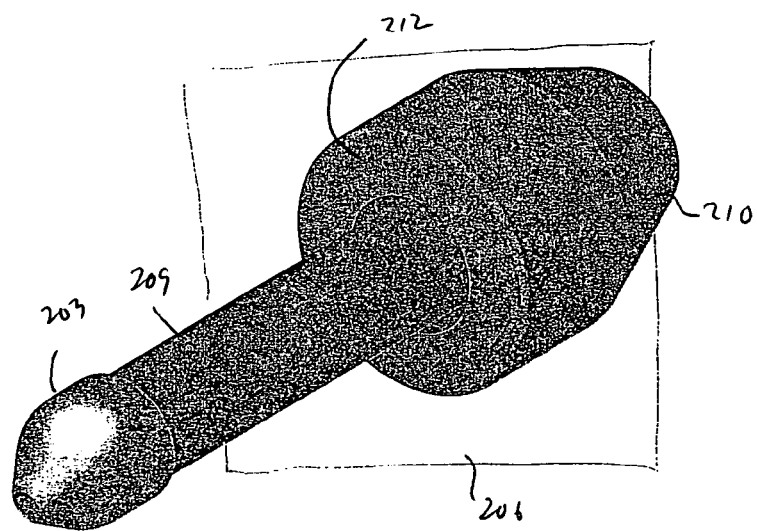
FIG. 45 is a perspective view, depicting a sixth step of employing its sensor delivery system of FIG. 39.
Figure 46:
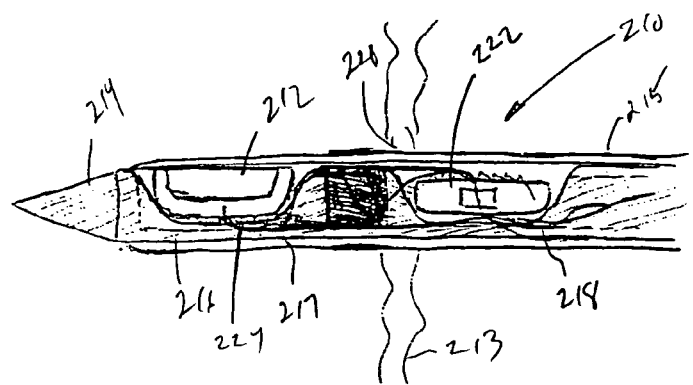
FIG. 46 is a cross-sectional view, depicting a first step of employing a sensor delivery system including dual chambers.
Figure 47:
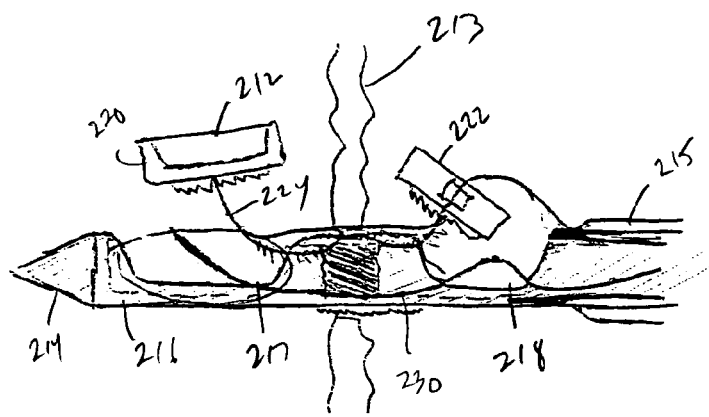
FIG. 47 is a cross-sectional view, depicting a second step of employing a sensor delivery system including dual chambers.

In yet another approach (See FIGS. 39-45), an elongate sensor delivery system 202 can include a terminal end 203 having a retractable, sharpened tip or needle 204 that can aid in puncturing a hole 205 through target tissue 206 or other structure such as a graft. When in its fully assembled configuration, a first longitudinally retractable sleeve 208 extends to the terminal end 203 and upon withdrawal (See FIGS. 42 and 43) exposes a housing 209 that houses the sensor assembly. In one contemplated embodiment, the housing 209 can be made from nitinol and include expanding fingers (not shown) which are configured to engage a far side of the target tissue.

Once the first retractable sheath 208 is fully withdrawn, a collar 210 equipped with one component of a conventional ratcheting mechanism cooperating with an inferior portion 211 of the housing 209 can be advanced until a superior end 212 of the collar 210 engages a near side of the target tissue 206 and is locked in place. To accomplish this advancement of the collar 210, the delivery assembly 202 can be equipped with a second longitudinally moveable sleeve 214. Moreover, it is intended that the superior end 212 of the collar 210 include sealing promoting materials that achieve closure of the puncture site 205. A conventional releasable engagement (such as a threaded or spring release) between the sensor having 209 and the remainder of the delivery apparatus 202 allows for the complete removal of the delivery apparatus from the interventional site.

A dual chamber sensor delivery system 210 (See FIGS. 46-51) can also be employed to affix a sensor 212 to a far side of a target tissue 213 or a graft wall, for example. The dual chamber delivery system 210 has an elongate profile and a pointed terminal end portion 214. A retractable sleeve 215 encases a main catheter component 216 including a first 217 and a second chamber 218 spaced longitudinally along a common side of superior portion of the main component 216.

When assembled, configured within the first chamber is a first sensor assembly component 220 carrying the sensor 212. A second sensor assembly component 222 is similarly configured within the second chamber. Attached to a side of the first sensor assembly component 220 is a wire 224 which is threaded through a bore passing through the second sensor assembly component 222 and extends in an inferior direction to an operator through an elongate tubular member 226. The elongate tubular member 226 is longitudinally movable with respect to the retractable sheath 215 and is contained within the sheath 215 along side the main catheter 216 (See FIG. 48). Additionally, each sensor component includes teeth or other tissue engagement structure 227 that aids in affixation to the target tissue 213 (FIG. 50) as well as internal silicone seals 229 (FIG. 51) for closing the puncture site 228 and seal promoting features.

In use, the dual chamber sensor delivery system 210 is advanced from outside a patient's body to within the patient to the target tissue or other wall structure 213. The system 210 is passed through a hole or puncture site 228 (See FIG. 46) formed by the system 210 or any of the other previously described structures so that the first sensor assembly component 220 resides on the far side of the target tissue and the second sensor assembly 222 component is on the near side. The sheath 215 is then withdrawn to expose the sensor components 220, 222 (FIG. 47) and an ejection wire 230 made from nitinol or other suitable material is manipulated to cause the sensor component 220, 222 to be ejected from the first and second chambers 217, 218, respectively.

Figure 48:
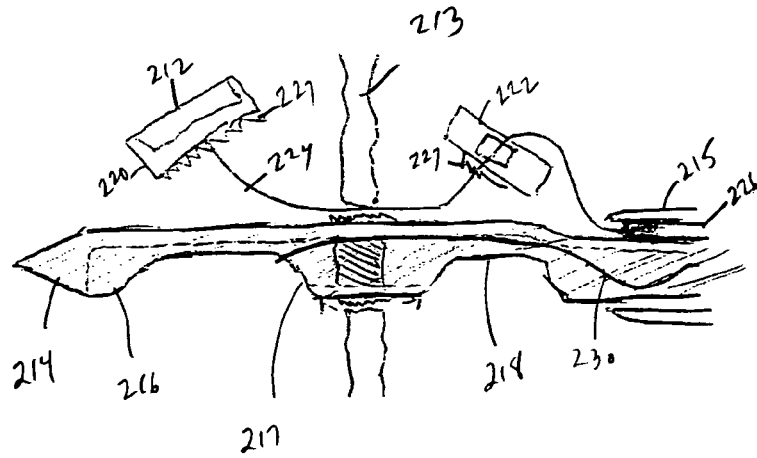
FIG. 48 is a cross-sectional view, depicting a third step of employing a sensor delivery system including dual chambers.
Figure 49:
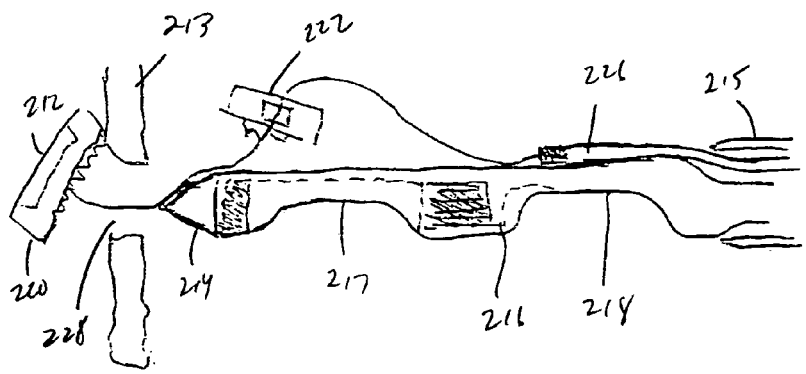
FIG. 49 is a cross-sectional view, depicting a fourth step of employing a sensor delivery system including dual chambers.
Figure 50:
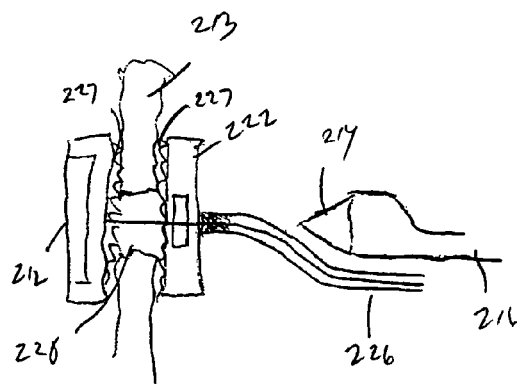
FIG. 50 is a cross-sectional view, depicting a fifth step of employing a sensor delivery system including dual chambers.
Figure 51:
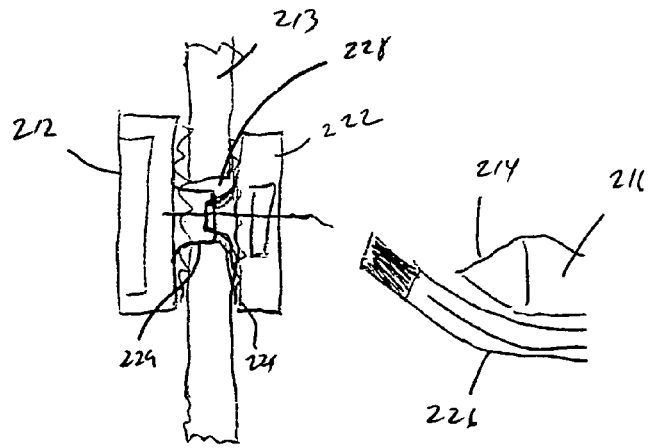
FIG. 51 is a cross-sectional view, depicting a sixth step of employing a sensor delivery system including dual chambers.

Next, the main catheter 216 is rotated to clear the sensor components 220, 222 from the chambers 217, 218 while the relative positioning of the elongate tubular member 226 housing the wire 224 is maintained (FIG. 48).

Thereafter, the main catheter 216 is withdrawn and the elongate member 226 is advanced (FIGS. 49 and 50) to cause the first and second sensor assembly components to be placed in opposition with opposing sides of the target structure 213. When so positioned, the wall engaging structure 227 of the sensor components aid to permanently affix the devices against the target structure, the second component 222 acting as a locking plug. Moreover, by applying a sufficient withdrawal force upon the wire, the silicone seal 229 of the first sensor component is drawn into and fills one side of the puncture site 228 and by applying sufficient forward force to the elongate member 226, the silicone seal 229 of the second sensor component fills another side of the puncture site. Finally, the wire 224 is severed or otherwise released from engagement to the first sensor assembly component 220, leaving the sensor 212 permanently in place at the target site 213. The main catheter 216 and elongate tubular member 226 are of course removed from the patient and any incisions are closed.

Figure 52:
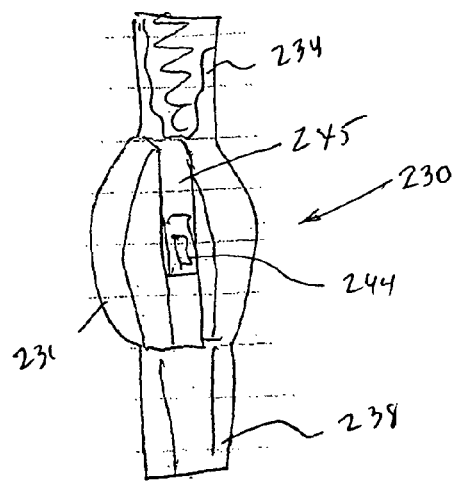
FIG. 52 is a side view, depicting a sensor having threaded structures.
Figure 53:
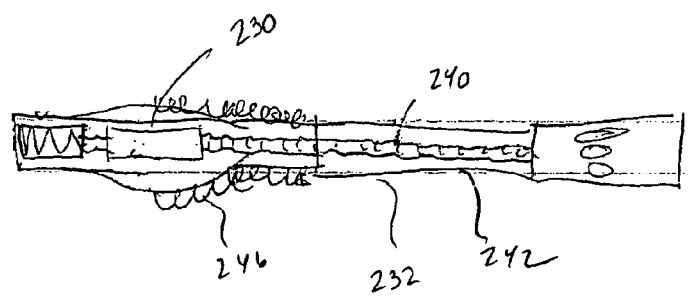
FIG. 53 is a cross-sectional view, depicting a first step of employing a delivery catheter carrying the sensor of FIG. 52.
Figure 54:
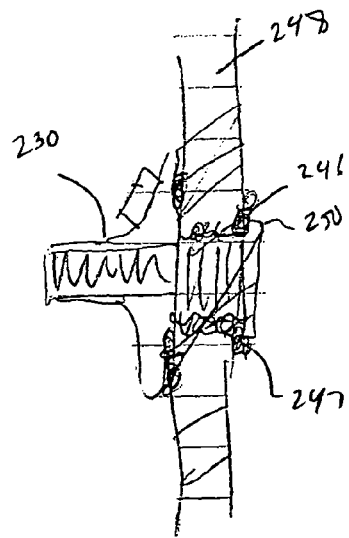
FIG. 54 is a cross-sectional view, depicting the sensor of FIG. 52 implanted at an interventional site.
Figure 63:
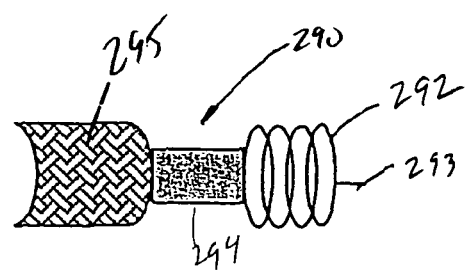
FIG. 63 is a side view, depicting a sensor including a mesh pad and helical coil.

Turning now to FIGS. 52-54, there is shown a threaded sensor assembly 230 and a delivery catheter 232 therefor. In operation, the threaded sensor 230 performs something like a dry-wall nut and the delivery catheter 232 like a fastener. The threaded sensor assembly 230 includes a threaded superior end portion 234, an expandable mid-section cage 236, and an inferior portion 238. An internal bore extends through the device providing a space for a screw 240 running through an outer sheath 242 of the delivery catheter 232 (Shown retracted in FIG. 53). Also, a sensing device 244 is placed or affixed to one rib 245 of the expandable cage 236 and fuzz material or rubber or plastic 246 material can be attached to the body of the threaded sensor assembly 230. Various alloys or plastic materials can be used for the sensor assembly body or carrier which can also be coated with a drug for the delivery of the same.

Whether simply plugging a puncture 247 or for the purpose of placing a sensor adjacent target tissue or other structure or medical device 248, the delivery catheter 232 is placed in the vicinity of the target and then through the puncture or opening 247 therein. Once the superior end portion 234 and midsection 236 are placed beyond the far side of the target, the sheath 240 is withdrawn to expose the sensor assembly 230. Next, the catheter 232 is held longitudinally stationary while the internal screw device 240 is rotated to thereby expand the midsection cage 236.

This action is continued until the ribs 245 are collapsed against the far side of the target structure, the rear side of the tissue being engaged by a terminal end 250 of the inferior portion 238 (which can be flanged or include a collar) of the sensor assembly 230. A seal is created at the puncture site via the body of the sensor assembly 230 as well as the fuzzy or other material 247 attached to the sensor body. Release of the sensor assembly 230 from the catheter can be accomplished by rotating the screw device in a direction opposite to that which causes the expansion of the sensor body or by other known methods or devices.

In a related approach (FIG. 55), another embodiment of a threaded sensor assembly 252 can include a sharpened terminal end 254 as well as a superior 256 and inferior 258 portions that collapse about opposite sides of target tissue or structure 259. A sensing device 260 is positioned on the superior portion 256 and the inferior end portion 258 includes a cap structure 261 defining a releasable connection to a delivery catheter having a screw device 262.

Significantly, the sensor assembly 252 can include a body formed from silicone tubing for the purpose of providing an atraumatic surface engaging the target structure. In one particular aspect, the tubing could be configured to include a side or coaxial lumen to be filled with a medium of air or liquid for inflation to promote sealing at a puncture site.

Various other sensor assemblies and delivery catheters are shown in FIGS. 56-65. As shown in FIGS. 56 and 57, a sensing device 270 can form a superior end of a delivery catheter 272. When placed across target tissue or other structure 274, the delivery catheter 272 can be removed, leaving the sensing device implanted. The sensing device 270 can have a pointed terminal end 275, a capsule 276 that retains a sensor and an inferior portion 277 that is releasably connected to the delivery catheter 272 and which traverses the target tissue. As seen in FIGS. 58 and 59, an alternative embodiment of a sensing device 280 can have a sensor attached to a pointed terminal end thereof and can lack any substantial inferior portion extending inferior to target tissue 274. In each embodiment, the portion of the sensor assemblies extend beyond the target tissue 274 to thereby provide a space between the target tissue 274 and the sensor of the sensing devices.

In yet another aspect, the sensing device can include clamps 284 (See FIGS. 60-62) which engage an inferior side of a target tissue or other structure 274 upon placement of a sensor 286 beyond the target tissue 274. An access tube 288 of any of the various previously described devices can be employed to accomplish the implantation of the sensor device adjacent the target tissue. Another approach (See FIG. 63) involves equipping another embodiment of a sensing device 290 with a helical coil 292 with a sharp leading edge that facilitates driving the device across target tissue. A sensor 294 is attached to a back end of the helical coil 292 followed by a mesh pad 295 designed to fill the opening created by the coil. The mesh pad 295 is contemplated to be pre-treated where desired with a clotting agent to speed sealing the opening.

Figure 64:
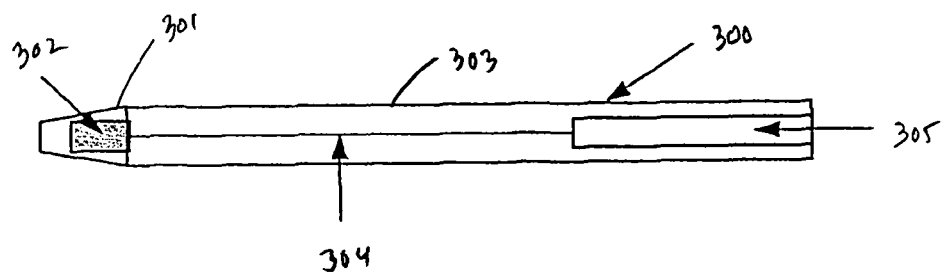
FIG. 64 is a side view, depicting a delivery catheter for the sensor of FIG. 63.
Figure 65:
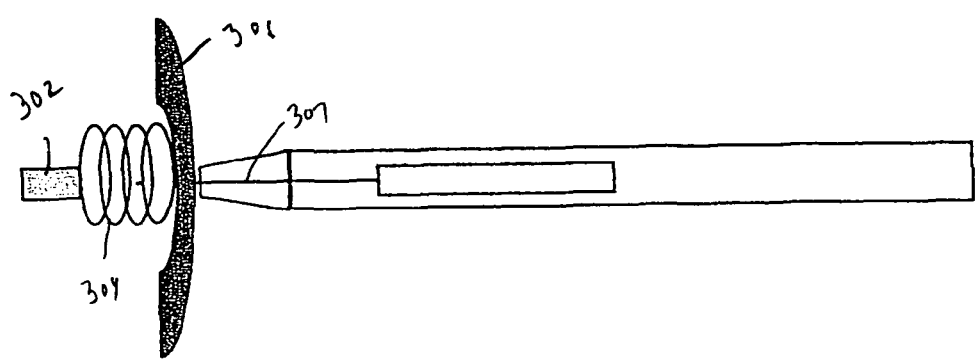
FIG. 65 is a side view, depicting an intermediate step of employing the delivery catheter of FIG. 64 to release the device of FIG. 63.
Figure 66:
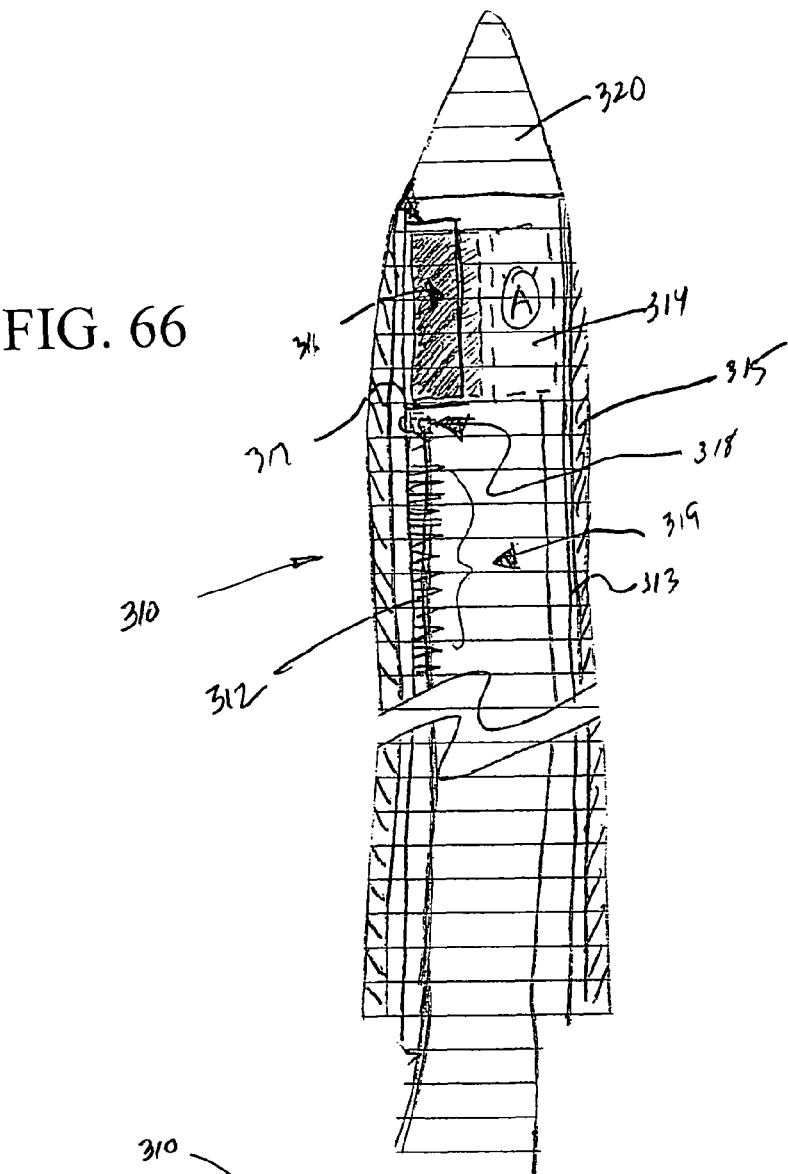
FIG. 66 is a cross-sectional view, depicting a sensor delivery system including a spring ejector mechanism.
Figure 67:
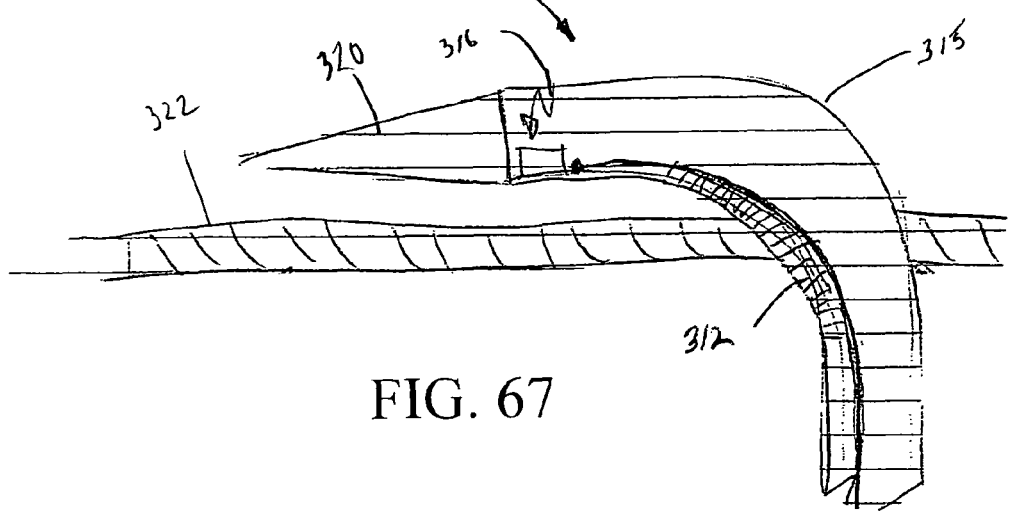
FIG. 67 is a cross-sectional view, depicting the sensor delivery system of FIG. 66 in use.
Figure 71:
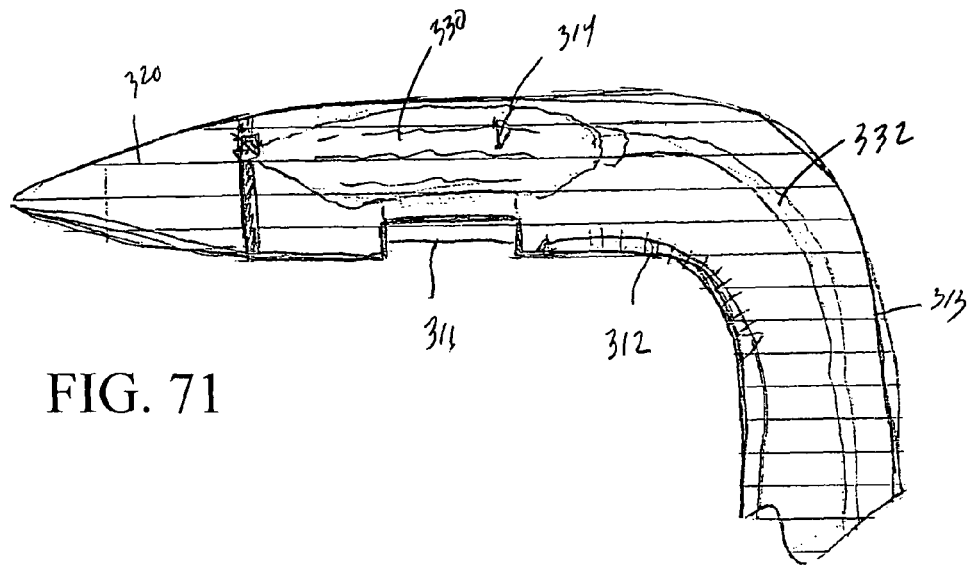
FIG. 71 is a cross-sectional view, depicting a superior end portion of a sensor delivery catheter equipped with a balloon ejection system.
Figure 72:
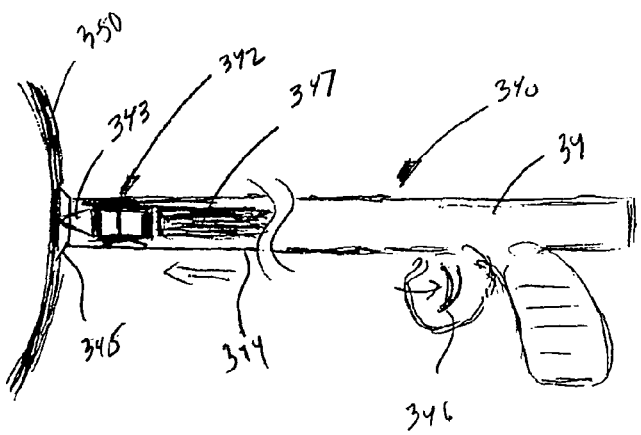
FIG. 72 is a partial cross-sectional view, depicting another sensor deployment device.
Figure 73:
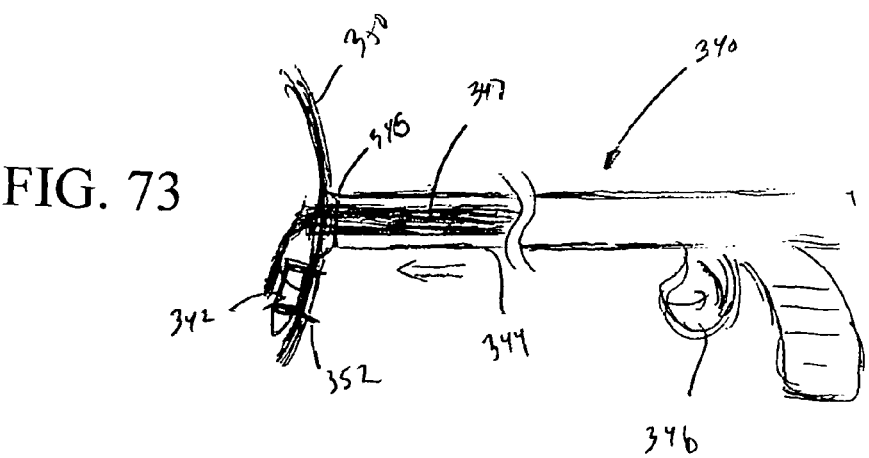
FIG. 73 is a partial cross-sectional view, depicting use of the sensor deployment device of FIG. 72.

Referring now to FIGS. 64 and 65, there is shown a sensor delivery catheter 300 having a superior end portion 310 for receiving a sensing device 302, a midsection 303 that accepts the length of a loaded, straightened coil 304 and a pusher 305. The pusher 305 is contemplated to facilitate advancing the sensing device 302 beyond target tissue 306. Once beyond the target tissue, the straightened coil 304 is designed to resume a helical configuration to thereby route the sensor 302 a desired distance beyond the target tissue. An inferior portion 307 of the coil 304 is permitted to extend through and reside on a near side of the target tissue to thereby hold the sensing device 302 in place. As with each of the previous embodiments, the catheter can be employed to deliver a sensor beyond any structure including walls defining a graft.

In certain circumstances, it may be advantageous to combine aspects of a steering catheter with a sensor delivery system. Various approaches are contemplated, particular embodiments of which are shown in FIGS. 66-73. One embodiment of a steerable sensor delivery system 310 (FIGS. 66 and 67) includes a steering wire 312, a main catheter 313, an ejection system 314 and an outer sheath assembly 315. The main catheter 313 further includes a superior end portion configured to receive a sensor 316 and which is equipped with a cut-out 317 through which the sensor 316 is ejected from the main catheter 313.

When in an assembled form, the main catheter 313 houses the steering wire 312 which is attached to a wall of the main catheter at a point 318 inferior the cut-out 317. As with conventional steering wires, a superior portion thereof 319 accomplishes the steering function. The superior portion 319 can include any structure which accomplishes the bending or curving of the catheter 313 such as a two wire system or side cut-outs or the like which are brought together causing it to bend externally through the manipulation of the steering wire 312. The outer sheath 315 surrounds the main catheter 313 and is retractable with respect thereto. The main catheter 313 can further include a terminal end cap 320 having a tapered or conical profile.

In use, the terminal end 320 and superior portion of the steerable sensor delivery catheter 310 can be passed through a vessel wall or other target tissue or structure 322. When so positioned inferior end portions (not shown) of the steering wire 312 can be manipulated to cause lateral movement of the main catheter 313. Through necessary positioning and/or rotation of the main catheter 313, the sensor 316 is positioned adjacent tissue intended for implantation.

Ejection of the sensor 316 from the main catheter 313 can be accomplished in a number of ways. In one approach (FIGS. 68-70), the sensor delivery system 310 is equipped with a release wire 324 and the main catheter 313 includes a pair of exit ports 325. The ejection system 314 includes a sensor engaging platform 326 extending from which are a couple of rods 327. A spring 328 is configured about each rod 327 and each rod further includes a through hole 329. When in an assembled configuration, the ejection system 214 is held in a retracted position by threading the release wire 314 through the exit ports 325 of the main catheter 313 and through the holes 329 of the rods 327 extending from the sensor platform 326. The springs 328 are in turn held in a compressed configuration and store the energy to eject the sensor 316 from the main catheter 313.

Subsequent to passing the main catheter 313 through a target tissue 322, the steering wire 312 is manipulated to cause the main catheter 313 to be oriented such that the sensor 316 is placed adjacent an implantation site. Thereafter, the release wire 324 is withdrawn from engagement with the ejection system 314 thereby allowing the spring 328 to force the sensor platform 326 to eject the sensor 316 from the main catheter 313.

In an alternate approach (See FIG. 71), the ejection system 314 can comprise an inflatable balloon 330 attached to the end of an inflation lumen 332. When advanced to target structure, the balloon 330 is held in a deflated configuration. Once access to the target is obtained, if necessary, the steering wire 312 is manipulated to position a sensor 316 loaded in the main catheter 313 as desired. Next, the balloon 330 is inflated to cause the ejection and implantation of the sensor at a target site.

In a further aspect (See FIGS. 72 and 73), a sensor delivery system 340 for implanting a sensor assembly 342 having a nose cone 343 includes a handle assembly having an elongate barrel 344 with a split diaphragm terminal end 345. The barrel 344 is intended to extend from exterior a patient to an implantation site. The split diaphragm provides an atraumatic surface for engaging the target tissue or other structure as well as a working space through which the nose cone 343 of the sensor 342 is intended to be ejected.

The handle assembly of the sensor delivery system 340 further includes a trigger 346 that is operationally connected to a pusher assembly 347 that is intended to cause the sensor 342 to be ejected through the split diaphragm 345. That is, pulling the trigger 346 causes the pusher assembly 347 to advance and place the sensor in a superior direction and ultimately be ejected from the barrel 344. As the sensor 342 is so ejected, the nose cone 345 of the sensor breaches the target structure 350. By employing one of the previously described steering mechanisms, the sensor can be caused to be placed adjacent and implanted at a target site.

Figure 74:
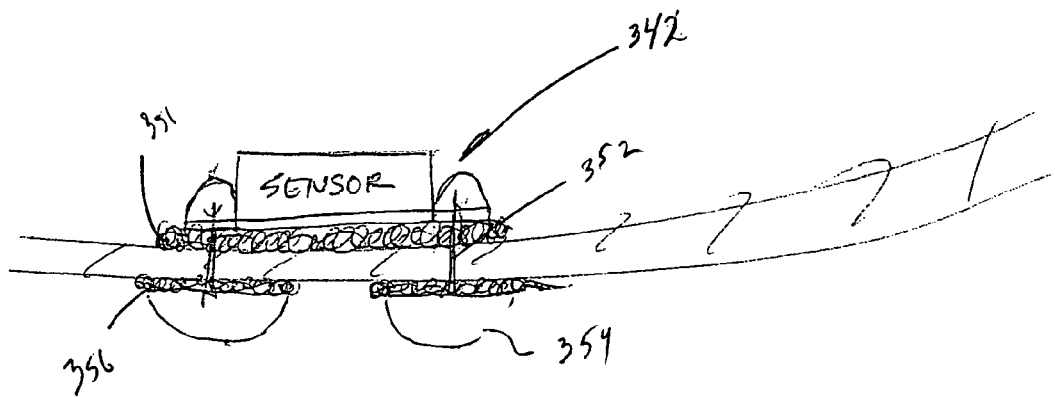
FIG. 74 is a cross-sectional view, depicting an implantable sensor equipped with locking pins.
Figure 75:
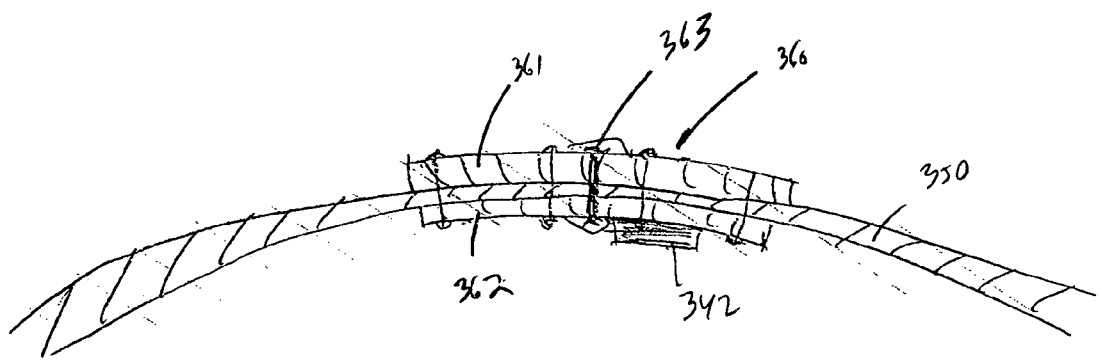
FIG. 75 is a cross-sectional view, depicting an implantable sensor equipped attachment patches.

One of several methods can be employed to cause the sensor 342 to be retained against target tissue. The sensor 342 can be equipped with barbs or pins 352 (See FIG. 73) alone or can further cooperate with self locking caps 354 (See FIG. 74) that engage the barbs 352. The sensor assembly 342 can further include pliable material 356 for cushioning the target tissue and to aid in the healing and sealing process. Moreover, the caps can include one-way spring clips and the barbs or pins 352 can be serrated or grooved to aid in maintaining engagement between the component parts. It is contemplated that the self-locking caps 354 can be delivered to the target site via a separate catheter or the original delivery catheter.

In yet another aspect, the target site 350 can first be configured with a patch assembly 360 for the purpose of aiding in reducing the likelihood of tearing at the target site. That is, a patch assembly 360 includes a first patch 361 configured to be placed on a near side of target tissue or wall 350 and a second patch 362 for placement on the far side of the target tissue or wall 350 can be utilized to prepare a sensor delivery site. The patent assembly 360 further is contemplated to include a one way gate 363 through which a sensor 342 can be placed and ultimately be implanted on the far side of the tissue. Locking pins like those previously described can be provided to hold the assembly together.

Various approaches have been described herein to place sensors on target tissue or grafts or other structure for the purpose of monitoring desired parameters in an area of interest. It is to be recognized that whereas the disclosed embodiments have been described as having certain structure, the components can be stored and incorporated into other embodiments as needed.

We claim:

1. A system comprising:
an elongate tubular member having a first lumen and a second lumen longitudinally enclosed therein, the first lumen configured to provide a vacuum through a valve associated with an inferior end into the first lumen formed within an annular interior of an outside wall of the elongate tubular member and the second lumen located axially interior to the first lumen and extending a total length of an inside of the elongate tubular member that is configured at a superior end to isolate a puncture in an exterior of a body cavity from the vacuum applied through the valve;
the elongate tubular member having a terminal end portion, associated with the superior end and delivered through the longitudinally enclosed second lumen, that is configured to engage the exterior of the body cavity from the interior and having a means for sealing the puncture in the exterior of the body cavity from the interior; and
an inner member coaxially received within the second lumen of the elongate tubular member along with the terminal end portion;
wherein the inner member comprises a wall puncturing assembly.

2. The system of claim 1, wherein the inner member further comprises a sensor delivery assembly.

3. The system of claim 2, wherein the sensor delivery assembly includes a sensor.

4. The system of claim 3, wherein the sensor includes a body and expandable structure attached to the body.

5. The system of claim 3, wherein the sensor includes a guide for advancing the sensor along a wire.

6. The system of claim 3, wherein the sensor delivery assembly includes a cannula that receives the sensor, the cannula having an internal bore which follows the contours of the sensor.

7. The system of claim 1, wherein the terminal end includes flexible walls providing an enlarged foot print and a sealing engagement when placed against the exterior of the body cavity.

8. The system of claim 1, wherein the wall puncturing assembly comprises a wall puncturing member.

9. The system of claim 8, wherein the puncturing member is retractable.

10. The system of claim 8, wherein the wall puncturing member is attached to and configured beyond a far end of the elongate tubular member.

* * * * *